United States Patent [19]

Hunter

[11] Patent Number: 4,937,070

[45] Date of Patent: Jun. 26, 1990

[54] METHODS AND COMPOSITIONS FOR TREATMENT OF PATHOLOGICAL HYDROPHOBIC INTERACTIONS IN BIOLOGICAL FLUIDS

[75] Inventor: Robert L. Hunter, Tucker, Ga.

[73] Assignee: Emory University, Atlanta, Ga.

[21] Appl. No.: 433,008

[22] Filed: Nov. 7, 1989

Related U.S. Application Data

[60] Division of Ser. No. 291,925, Dec. 29, 1988, Pat. No. 4,879,109, which is a continuation-in-part of Ser. No. 45,459, May 7, 1987, Pat. No. 4,801,452, which is a continuation-in-part of Ser. No. 43,888, Apr. 29, 1987, abandoned, which is a continuation of Ser. No. 863,582, May 15, 1986, abandoned.

[51] Int. Cl.$^5$ ............................................. A61K 31/745
[52] U.S. Cl. ........................................ 424/83; 514/833
[58] Field of Search ........................... 424/83; 514/833

[56] References Cited

U.S. PATENT DOCUMENTS

| | | | |
|---|---|---|---|
| 2,674,619 | 4/1954 | Lundsted | 560/198 |
| 2,854,378 | 9/1958 | Buckwalter | 514/152 |
| 3,089,818 | 5/1963 | Stone | 242/78 |
| 3,140,232 | 7/1964 | Noseworthy | 424/78 |
| 3,450,502 | 6/1970 | Hymes | 422/35 |
| 3,577,522 | 5/1971 | Hymes | 424/78 |
| 3,590,125 | 6/1971 | Hymes | 424/78 |
| 3,641,240 | 2/1972 | Hymes | 424/78 |
| 3,740,421 | 6/1973 | Schmolka | 424/65 |
| 3,867,521 | 2/1975 | Miskel | 424/37 |
| 3,956,259 | 5/1976 | Garcia | 428/423.3 |
| 3,980,772 | 9/1976 | Ginger | 424/94.3 |
| 4,073,886 | 2/1978 | Kehm | 530/833 |
| 4,100,271 | 7/1978 | Kreszanoski | 424/78 |
| 4,179,337 | 12/1979 | Davis | 435/181 |
| 4,186,253 | 1/1980 | Yokoyama | 435/240 |
| 4,305,922 | 12/1981 | Rhodes | 424/1 |
| 4,395,393 | 7/1983 | Schmolka | 424/78 |
| 4,407,790 | 10/1983 | Oakes | 424/78 |
| 4,600,652 | 7/1986 | Solomon | 428/423.3 |
| 4,609,546 | 9/1986 | Hiratani | 424/83 |

FOREIGN PATENT DOCUMENTS

| | | |
|---|---|---|
| 5094 | 6/1977 | Japan. |
| 8601747 | 8/1986 | PCT Int'l Appl. |
| 1183112 | 8/1983 | United Kingdom. |

OTHER PUBLICATIONS

Schmolka, I., "A Review Of Block Polymer Surfactants", *Journal of the American Oil Chemists Society*, 54, No. 3, pp. 110–116 (1977).

(List continued on next page.)

*Primary Examiner*—John W. Rollins
*Attorney, Agent, or Firm*—Jones, Askew & Lunsford

[57] ABSTRACT

In accordance with the present invention, a method and composition is provided for treating pathological hydrophobic interactions in biological fluids in which there is acute impairment of the circulation, especially the microcirculation. More particularly, the present invention relates to compositions and methods for treating circulatory diseases comprising using certain ethylene oxide-propylene oxide condensation surface active copolymers either alone or in combination other compounds.

Also contemplated in the present invention is a method for preserving a suspension of platelets. The method comprises adding an effective amount of a surface active copolymer.

The surface active copolymer can be an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably approximately 1750 to 3500, and b is an integer such that the hydrophile portion represented by $(C_2H_4O)$ constitutes approximately 50% to 95% by weight of the compound.

3 Claims, 3 Drawing Sheets

OTHER PUBLICATIONS

Block and Graft Copolymerization, vol. 2, (ed. by R. J. Ceresa, John Wiley & Sons, 1976) "The Applications of Block Copolymer Polyol Surfactants", L. G. Lundsted and I. R. Schmolka; pp. 174 through 205 and pp. 255 through 272 (references).

Reindorf, C. A., "Perfluorocarbon Compounds: Effects on the Rheological Properties of Sickle Erythrocytes in vitro", *American Journal of Hematology*, vol. 19, pp. 229–236 (1985).

Vercellote, G. M. "Activation of Plasma Complement by Perfluorocarbon Artifical Blood: Probable Mechanism of Adverse Pulmonary Reactions in Treated Patients and Rationale for Corticosteroid Prophylaxis", *Blood*, vol. 59, pp. 1299–1304 (1982).

Rodeheaver, G. T., "Pluronic F-68: A Promising New Skin Wound Cleanser", *Ann Emerg Med.*, 9:11, pp. 572–576 (1980).

Padilla, F., et al., "Effect of Flurocarbon Emulsions on the Mechanical Fragility of Normal and Sickle Cells:in Vitro Studies" Federation Proceedings, vol. 34, pp. 1510–1512 (1975).

Janoff, A. S., et al., "The Modification of Human Erythrocyte Membrane Structure by Membrane Stabilizers: An Electron Spin Resonance Study", *American Journal of Hematology* vol. 10, pp. 171–179 (1981).

Moore, A. R., et al., "Reduction of Splenic Vascular Resistance During Profusion By Pluronic F-68", *Journal of Surgical Research*, vol. 8, No. 12, pp. 563–566, (1968).

Benner, K. U. et al., "Cold-Induced Platelet Aggregation In Vivo And Its Inhibition By A Nonionic Surface Active Substance", *Thrombosis Research*, vol. 2, pp. 331–342, (1973).

Hymes, A. C., "The Influence Of An Industrial Surfactant Pluronic F-68, In the Treatment of Hemorrhagic Shock", *Journal of Surgical Research*, vol. 11, pp. 191–197, (1971).

Hoie, J., "Effects of Pluronic F68, Poloralkol, On Vascular Resistance in Vivo" *Journal of Surgical Research*, vol. 11, pp. 515–517, (1971).

Grover, F. L. et al., "A Nonionic Surfactant And Blood Viscosity", *Arch. Surg.*, vol. 106, pp. 307–310, (1973).

Grover, Frederick L. et al., "The Effect of Pluronic F-68 On Circulatory Dynamics And Renal And Carotid Artery Flow During Hemorrhagic Shock", *Journal of Surgical Research* vol. 17, pp. 30–35, (1974).

Ketchum, Lynn D. et al., "Pharmacological Alterations in the Clotting Mechanism: Use in Microvascular Surgery", *Journal of Hand Surgery*, vol. 3, pp. 407–415, (1978).

Ketchum, Lynn D. et al., "Experimental Use of Pluronic TM F-68 In Microvascular Surgery", *Plastic and Reconstructive Surgery*, vol. 53, pp. 288–292, (1974).

Vasco, K. A., et al., "Poloxalkol TM (Pluronic F-68): A Priming Solution for Cardiopulmonary Bypass", *Trans. Am. Soc. Artif. Int. Organs*, 18, 526–531 (1972).

Block, N. L., et al., "Acutely traumatized canine Ureter, Effects of Low Molecular Weight Dextran and Surfactant Pluronic F-68", *Urology*, vol. III 190–194, (1974).

Knize, D. M., "Use of Antisludging Agents in Experimental Cold Injuries", *Surgery, Gynecology & Obstetrics*, vol. 129, pp. 1019–1026, (1969).

Gaehtgens, et al., "Disaggregation of Human Red Blood Cells by Various Surface-Active Agents as Related to Changes of Cell Shape and Hemolysis", Act Heamat. vol. 33, pp. 82–89 (1975).

Smillie, et al., "Cryopreservation of Human Platelets with Polyvinylpyrrolidone" *Transfusion*, vol. 21, pp. 552 through 556, (1981).

Kunicki, et al., "A Study of Variable Affecting the Quality of Platelets Stored at Room Temperature", *Transfusion*, vol. 15, pp. 414 through 421, (1975).

Organ Perfusion and Preservation, (ed. by Norman, J. C., Appleton-Century-Crofts, (1968)), Paton, B. C., et al., "The Use of a Nonionic Detergent Added to Organ Perfusates" pp. 105 through 120.

Technical bulletin entitled "Performance Chemicals".

Technical bulletin entitled "Pluronic ® Block Copolymer Surfactants".

Perfluorochemical Blood Substitutes, Technical Information Ser. No. 5, Jun. 30, 1978, Revised, Jul. 1, 1981. Manufacturer: The Green Cross Corporation.

The Patent Cooperation Treaty International Search Report for PCT Patent Application No. PCT/US87/01067.

Patent Cooperation Treaty International Search Report for the PCT Patent Application No. PCT/US87/01747.

U.S. Patent Application Ser. No. 045,459 upon which priority for PCT Patent Application No. PCT/US87/01067 was based.

METHODS AND COMPOSITIONS FOR TREATMENT OF PATHOLOGICAL HYDROPHOBIC INTERACTIONS IN BIOLOGICAL FLUIDS

CROSS-REFERENCE TO RELATED APPLICATIONS

This application is a divisional patent application of U.S. patent application Ser. No. 291,925 filed on Dec. 29, 1988, now U.S. Pat. No. 4,879,109, which is a continuation-in-part of U.S. patent application Ser. No. 45,459 filed on May 7, 1987, now U.S. Pat. No. 4,801,452 issued on Jan. 31, 1989, which is a continuation-in-part of U.S. patent application Ser. No. 43,888 filed on Apr. 29, 1987, now abandoned, which is a continuation of U.S. patent application Ser. No. 863,582, now abandoned, filed on May 15, 1986.

TECHNICAL FIELD

The present invention relates to a method and composition for treating pathological hydrophobic interactions in which there is acute impairment of the circulation, especially the microcirculation. More particularly, the present invention relates to compositions and methods for treating circulatory diseases comprising using certain ethylene oxide-propylene oxide condensation copolymers either alone or in combination with other compounds, including but not limited to, fibrinolytic enzymes, anticoagulants, free radical scavengers, antiinflammatory agents, antibiotics, membrane stabilizers and/or perfusion media.

BACKGROUND OF THE INVENTION

The term "pathological hydrophobic interactions" means detrimental adhesion of components, including but not limited to, cells and molecules in blood or other biological fluids thereby slowing or stopping the flow of blood or other biological fluid. The term "fibrinolytic enzyme" menas any enzyme that is capable of cleaving fibrin or capable of causing fibrin to be cleaved. Enzymes that are capable of cleaving fibrin or causing fibrin to be cleaved include, but are not limited to, streptokinase, urokinase, tissue plasminogen activator (t-PA) produced from cell cultures, tissue plasminogen activator produced by recombinant DNA technology and plasminogen activator produced from prourokinase. The terms "isotonic" or "isoosmotic" solution are defined as solutions having the same osmotic pressure as blood. The term "SOD" means superoxide dismutase and refers to any enzyme capable of neutralizing oxygen radicals. The terms clot, fibrin clot and thrombus are used interchangeably. The term "microcirculation" means blood circulation through blood vessels that are about 50 microns in diameter or less. The term "soluble fibrin" means soluble high molecular weight polymers of fibrinogen and fibrin. The term "biological fluids" means blood, lymph, or other fluids found in animals or humans. The term "platelet suspension" means a suspension of platelets that has a higher concentration of platelets than that found in blood. The term "plasma extender" means any substance that can be added to animal or human blood to maintain or increase coloid osmotic pressure. The term "cytoprotective" as used herein, means an increased ability of myocardial, endothelial and other cells to withstand ischemia or recover from ischemia, or other noxious insults including but not limited to burns. The term "ischemic tissue" is any tissue that is damaged from reduced blood flow. The term "anticoagulant" is any compound or agent that inhibits the blood coagulation process. The term "reperfusion injury" means injury to tissue or cells which occurs during reperfusion of damaged tissue with blood. The term "damaged tissue" means tissue damaged by ischemia, burns, toxins or other noxious insult.

It is to be understood that the citation of art contained herein is in no way to be construed as an admission that said art is suitable reference against the present patent application nor should this citation act as a waiver of any rights to overcome said art which may be available to the applicant.

A number of reports have described high amounts of fibrinogen and/or soluble fibrin in the blood of patients with thrombosis, impending thrombosis and many other diseases. These conditions include acute or chronic infection, severe trauma, burns, sickle cell crisis, malaria, leukemia, myocardial infarction, sepsis, shock, and almost any serious illness which produces tissue damage or surgical maneuvers. Evidence indicates that the high concentrations of fibrinogen and/or soluble fibrin may play an important role in the pathology of the conditions. Furthermore, much of the pathology that is encountered in disease may be due to pathological hydrophobic interactions which may be at least partially mediated by high concentration of fibrinogen and/or soluble fibrin.

What is needed is a means of decreasing the adverse effects of soluble fibrin. This would involve blocking the adhesion of soluble fibrin to cells in the circulation thereby blocking the aggregation of such cells and their adhesion or friction to vessel walls in the microvasculature. This would also decrease the risk of thrombosis.

Each year about 550,000 Americans die from heart attacks. Even more—close to 700,000—have heart attacks and live. While a heart attack victim may survive, part of his or her heart will almost certainly die. The death of heart muscle, called myocardial infarction, is due to coronary artery thrombosis in 70-90% of the cases. When a thrombosis, or blood clot, occludes one of the arteries of the heart, it stops the flow of blood to the surrounding muscle which deprives it of oxygen and other nutrients. In the past, nothing could be done to reverse this process. The high technology devices in intensive care units mostly support patients so they can live while a portion of their heart dies.

Similar situations occur in many other tissues when the blood supply to the tissue is affected by a thrombus or embolus. Stroke, deep vein thrombosis and pulmonary embolus are examples. Typically, the clot forms and is not treated for a relatively long period of time. Blood flow distal to the clot is greatly diminished or is stopped completely. The tissue that is normally fed by that vessel will be severely damaged unless blood flow is reestablished in a short period of time.

It has been found that certain enzymes are able to degrade, initiate or activate other enzymes that can degrade fibrin deposits to open clogged arteries. The enzymes which have been used successfully include streptokinase, urokinase, prourokinase, tissue plasminogen activator produced from cell cultures and tissue plasminogen activator produced by recombinant DNA technology. These enzymes are most successful if administered shortly after the occlusion of the blood vessels before the heart tissue has sustained irreversible damage. In one study of 11,806 patients treated with intravenous or intracoronary artery streptokinase, an 18% improvement of survival was demonstrated. If the treatment was begun within one hour after the initial pain onset of the heart attack, the in-hospital mortality was reduced by 47%. (See *The Lancet*, Vol. 8478, p. 397–401, Feb. 22, 1986). It was demonstrated that early lysis of the thrombus resulted in salvage of a portion of heart tissue which would have otherwise have died. In studies using angiography to assess the patency of blood vessels, it was found that tissue plasminogen activator could completely open the vessels of 61% of the 129 patients versus 29% of controls who were not treated with the enzyme. (See Verstraete, et al., *The Lancet*, Vol. 8462, p. 965–969, Nov. 2, 1985). Tissue plasminogen activator requires the addition of approximately 100 $\mu l$ of Tween 80 per liter of solution to promote dispersion of the enzyme. (See Korninger, et al., *Thrombos, Haemostas*, (Stuttgart) Vol. 46(2), p. 561–565 (1981)).

The natural enzymes that lyse thrombi in vessels do so by activating fibrinolysis. Fibrin is the protein produced by polymerization of fibrinogen. It forms a gel which holds the thrombus together. The fibrin molecules which form clots gradually become cross-linked to make a more stable clot. All three enzymes, urokinase, streptokinase and tissue plasminogen activator, are effective because of their ability to activate an enzyme, plasmin, which degrades fibrin. Thus, they have similar effects on fibrin but they have different toxicities. If the fibrinolytic mechanisms (i.e., plasmin) are activated in the vicinity of a clot, the clot is lysed. If, however, they are activated systemically throughout the circulation, the body's capacity to stop bleeding or hemorrhage is markedly reduced. Streptokinase and urokinase tend to active systemic fibrinolysis. Consequently, they have been most effective when injected directly into the affected blood vessel.

Tissue plasminogen activator or t-PA, in contrast, becomes effective only when it is actually attached to fibrin. This means its activity is largely localized to the immediate area of a clot and does not produce systemic fibrinolysis. For this reason, tissue plasminogen activator is thought to produce less risk of hemorrhage than the other enzymes. If high does are used in an effort to increase the rate of clot lysis or to lyse refractory clots, then the amount of systemic fibrinolysis and risk of hemorrhage can become significant. t-PA can be injected intravenously into the general circulation. It circulates harmlessly until it contacts the fibrin in a blood clot where it becomes activated and causes the lyses of the clot. Tissue plasminogen activator is able to cause the lysis of a clot which is extensively cross-linked. This means it is possible to lyse clots which have been present for many hours.

Remarkable as the new enzyme therapies are, they are subject to serious complications and are not effective in all patients. Clots in the anterior descending branch of the left coronary artery are much more readily lysed than those in other arteries. If the enzyme is not delivered by the blood stream directly to the thrombus, it has no effect. For various reasons, more blood passes by or trickles around thrombi in the left anterior descending coronary artery than in the other major arteries. In addition, the presence of collateral circulation which forms in response to compromised blood flow in the major arteries adversely affects the rate of reopening or recanalization of the thrombosed major arteries. It is thought the presence of many collateral vessels which allow blood to bypass the clot reduces the pressure gradient across the clot. This in turn reduces the blood flow through the tiny openings which may persist in the clot, impedes the delivery of enzymes to the clot, and prevents the clot from being lysed.

Even after the clot has been lysed, the factors which led to the formation of the thrombus persist. This produces a high incidence of re-thrombosis and further infarction in the hours and days following lysis of the clot. Rethrombosis has been reported in between 3% and 30% of cases in which the initial treatment successfully lysed the clot. Anticoagulants are currently used to prevent the formation of new thrombi, but they tend to induce hemorrhage. There is a delicate balance between the amount of anticoagulation necessary to prevent re-thrombosis of the vessels and that which will produce serious hemorrhage.

A reported advantage of t-PA is its short half-life of less than 10 minutes, which may allow rapid reversal of bleeding problems should they occur. However, the clinical value of this consideration has not yet been demonstrated. Moreover, the short half-life may lead to an increased reocclusion rate following discontinuation of thrombolytic therapy, (See Williams, D. O., et al., "Intravenous recombinant tissue-type plasminogen activator in patients with acute myocardial infarction: a report from the NHLBI Thrombolysis in Myocardial Infarction Trial.", *Circulation* 1986; 73:338–46). To counter this problem, t-PA infusions have been continued for up to 6 hours in phase II of the TIMI (Thrombolysis in Myocardial Infarction Trial). Whether this will effectively reduce the incidence of reocclusion without increased bleeding remains to be proven. Although active thrombolysis ceases shorly after discontinuing administration of t-PA, it takes several hours to replace fibrinogen, so that the risk of continued bleeding does not terminate when t-PA is stopped. (See Rich, M. W., "tPA: Is it worth the price?", *American Heart Journal*, 1987, Vol. 114:1259–1261.

Finally, dissolving the clot after irreversible damage has taken place has little effect. The irreversible damage could be either to the heart muscle or vascular bed of the tissue supplied by the blood vessel. Once a cell is dead, the change is irreversible. However, the term irreversible damage is frequently applied to tissue in which a chain of events leading to cell death has been initiated, even though most cells are not yet dead. If this chain of events were broken, for example by restoring the microvasculature blood supply or stabilizing fragile membranes, then many cells could be saved. A major problem in widespread implementation of this new enzyme therapy is to find ways of identifying and treating the patients earlier in their disease and to find ways to make the treatment effective for a longer period of time after the initiation of thrombosis.

Animal studies have provided a better understanding of the events which control blood flow and tissue death following coronary artery thrombosis. Much of the heart muscle receives blood from more than one vessel. For this and other reasons, the tissue changes following a coronary thrombosis are divided into distinct zones. The central zone of tissue, i.e., usually that zone of tissue closest to the thrombus, becomes almost completely necrotic. This is surrounded by an area of severe ischemia. Outside this is an area of lesser ischemia called the marginal zone. Finally, there is a jeopardized zone which surrounds the entire area.

In studies with baboons, the central necrotic area was not affected by recanalization of the vessel after several hours. However, muscle in the other zones which had undergone less severe damage during the ischemic period could be salvaged. A surprising finding was that lysing of the thrombus to produce a perfect arteriograph was insufficient to restore normal flow in the majority of animals. (See Flameng, et al, *J. Clin. Invest.*, Vol. 75, p. 84–90, 1985). Some further impediment to flow had developed in the area supplied by the vessel during the time that it was occluded. In further studies, it was demonstrated that immediately after removing the obstruction to the vessel, the flow through the damaged tissue began at a high rate. However, within a short time the blood flow through the ischemic zone decreased and the tissue died.

Consequently, the regional blood flow immediately after reperfusion is a poor predictor of the salvage of myocardial tissue. If the blood flow through the damaged tissue remained near the normal levels, the success of tissue salvage was much greater. Hemorrhage occurred almost exclusively in the severely ischemic zone reflecting damage to the small blood vessels. The hemorrhage, however, remained limited to the severly ischemic tissue and did not cause extension of the infarction or other serious complication. Therapies which could preserve the blood flow through the small blood vessels distal to the major area of thrombus after reperfusion could be expected to markedly increase the salvage of myocardial tissue.

The damage to heart muscle cells which occurs after lysing the thrombus is due to other factors as well as ischemia. Contact of fresh blood with damaged or dead cells induces the influx of neutrophils, or pus cells, which can damage or kill heart cells which would otherwise have recovered. Much of the damage caused by neutrophils has been attributed to superoxide ions. (For a general review, please see "Oxygen Radicals and Tissue Injury" *Proceedings of a Brook Lodge Symposium*, Augusta Michigan, Barry Halliwell, Ed.). The superoxide anion can damage tissue in several ways. The interaction of the superoxide anion with hydrogen peroxide leads to the production of hydroxyl radicals which are highly toxic and react rapidly with most organic molecules. Mannitol is a selective scavenger of hydroxyl radicals. The enzyme, superoxide dismutase, catalyzes the decomposition of the superoxide anion. Enzymes such as superoxide dismutase, free radical scavengers or agents which prevent the influx on neutrophils are able to increase the salvage of heart muscle cells.

Continuing therapy is needed even after restoration of blood flow and salvage of damaged tissue. The arteriosclerosis that caused the original heart attack remains. American and European researchers have have found that arteriosclerosis still narrows the arteries in 70–80% of patients whose clots were lysed by thrombolytic therapy. Many physicians believe this obstruction must be opened for long term benefits.

Balloon angioplasty is a procedure whereby a catheter with a small balloon is inserted into the narrowed artery. The ballon is inflated, compresses the the atherosclerotic plaque against the vessel wall and dilates the artery. The effectiveness of this procedure is limited by the effects of ischemia produced by the ballon, by embolization of atheromatous material which lodges in distal vessels and by an increased tendency for immediate or delayed thrombosis in the area damaged by the balloon. The ballon tears the tissue exposing underlying collagen and lipid substances which induce formation of thrombi. The thrombus may occlude the vessel immediately or set up a sequence of events which leads to occlusion many days or weeks later. In addition, there is an interruption of blood flow to the heart tissue when the balloon is inflated. When the blood flow is interrupted, tissue downstream from the balloon is deprived of blood and can be damaged. Balloon angioplasty is representative of numerous clinical and experimental procedures for repairing the lumen of diseased arteries and vessels.

What is needed is a means of rendering the surface of the dilated vessel less thrombogenic, improving the blood flow through the distal tissue and breaking the embolized material into smaller pieces which are less likely to produce embolic damage. A means of restoring blood flow through the microcapillaries downstream from the site of balloon inflation is also required.

Another area where fibrinogen/fibrin plays a role is tumors. There is now strong evidence that fibrinogen-related proteins are localized in solid tumors. The anatomical distribution of fibrin in tumors varies depending on the tumor type. In carcinomas, fibrin is deposited in the tumor stroma and around tumor nests and may be particularly abundant toward the tumor periphery and at the tumor host interface. By contrast, fibrin is often less prominent in older, more central tumor stroma characterized by sclerotic collagen deposits. Fibrin may also be found between individual carcinoma cells. In some, but not all such cases, interepithelial fibrin deposits are related to zones of tumor necrosis; however, zones of tumor necrosis are not necessarily sites of fibrin deposition. Fibrin deposition in sacomas has been less carefully studied than that in carcinomas. In lymphomas, fibrin deposits may be observed between individual malignant tumor cells as well as between adjacent, apparently reactive benign lymphoid elements. Fibrin has been reported to appear in zones of tumor sclerosis, as in Hodgkin's disease. Research has indicated that the pattern and extent of fibrin deposition are characteristic for a given tumor. (See *Hemostasis and Thrombosis, Basic Principles and Clinical Practice*, "Abnormalities of Hemostasis in Malignancy", pp. 1145–1157, ed. by R. W. Colman, et al., J. B. Lippincott Company, 1987).

The lack of a uniform vascular supply to tumors can impede diagnostic and therapeutic procedures. For example, hypoxic tumors are less susceptible to many drugs and to radiation. Conventional drugs and new drugs, such as monoclonal antibody conjugates, are not effective unless they are delivered to tumor cells. Fibrin deposits that surround some types of tumors inhibit delivery of the drugs to the tumor. The blood supply of tumors is further compromised by other factors as well. Blood vessels in tumors are frequently small and tortuous. The hydrodynamic resistance of such channels further impedes the flow of blood to tumors.

Finally, lipid material on the atherosclerotic wall contributes to the bulk of the plaque which narrows the lumen of the artery and produces a highly thrombogenic surface. What is needed is a method of extracting or covering lipids from atherosclerotic plaques which leaves their surfaces less thrombogenic and reduces their bulk.

Use of copolymers prepared by the condensation of ethylene oxide and propylene oxide to treat an embolus or a thrombus has been described (See U.S. Pat. No. 3,641,240). However, the effect is limited to recently formed, small (preferably microscopic) thrombi and emboli which are composed primarily of platelets. To be effective, the compound must be used within 20 minutes after the initiation of thrombosis.

The use of the ethylene oxide and propylene oxide copolymer has little or no effect on a clot in a patient who has suffered a severe coronary infarction because such patients almost never receive treatment within 20 minutes following initiation of thrombosis. It is likely that many persons do not develop symptoms until the thrombus reaches considerable size. The clots that are occluding the blood vessel in these patients are large and stable clots. Stable clots are clots in which the fibrin has undergone cross linking. Fibrin which has undergone crosslinking is not effected by presence of the ethylene oxide-propylene oxide copolymers. The copolymers only affect new clots composed primarily of platelets in which the newly formed fibrin has not crosslinked.

Another problem that commonly occurs in damaged tissue where blood flow is interrupted is a phenomenon called "no reflow" phenomenon. This is a conditions wherein blood flow is interrupted to a tissue. When blood flow is restarted, such as after a clot is removed, flow in the smaller microcapillaries is often impaired because blood cells tend to clump in the microcapillaries thereby inhibiting flow of blood to the tissue. This can result in damage to the tissue.

In addition, such a composition would be useful in removing clots from solid tumors, increasing flow through tortuous channels and thereby allow delivery of therapeutic drugs to the tumor.

A further need is a composition that can be used to prevent or treat "no reflow" phenomenon. Such a composition should be capable of causing blood to flow in tissue after blood flow has stopped thereby preventing tissue damage.

Increased demand for platelet concentrates to treat bleeding associated with thrombocytopenia has prompted the need to determine optimal methods of storing platelets prior to transfusing them into a patient.

Viability, as measured by survival of $^{51}CR$-labeled platelets, seems best preserved when stored at 22° C., whereas platelet function, as measured by the ability of platelets to aggregate in response to epinephrine, collagen, and adenosine diphosphate is better preserved at 4° C. Platelets stored at room temperature for 48 to 72 hours as well as those kept refrigerated for 24 to 48 hours have been found by different investigators to produce satisfactory increases in platelet levels when transfused to thombocytopenic patients.

Thus, blood blanks wishing to store platelets prior to their transfusion into a patient are faced with the dilemma of whether they should be kept at room temperature, thus preserving their lifespan but possibly compromising their functional capacity, or whether they should be stored in the approximately 4° C. with the resultant preservation of function but shortening of post-transfusion survival time.

What is needed is a composition and method which can be added to a suspension of platelets which will preserve both lifespan and function of the platelets so that the platelet suspension can be stored for longer periods of time. Such a composition should also be capable of inhibiting the aggregation or clumping of platelets in the suspension.

Finally, the present inventor has identified a phenomenon called pathological hydrophobic interactions between blood components and those cells which line the blood vessels. This phenomenon is typically encountered when tissue is damaged in some manner. These pathological hydrophobic interactions cause blood flow to be reduced or stopped thereby causing damage to surrounding tissue. What is needed is a composition and method for reducing the pathological hydrophobic interactions and thereby allowing blood to flow into the damaged tissue.

SUMMARY OF THE INVENTION

In accordance with the present invention, a method is provided for treating pathologic hydrophobic interactions in blood and other biological fluids. In particular, the method of the present invention limits or prevents damage due to (1) high concentrations of hydrophobic soluble fibrin, (2) cell damage due to the exposing of hydrophobic domains in the cell membrane that are usually hidden or buried. The method of the present invention also has a cytoprotective effect.

The method of the present invention increases flow of biological fluids in diseased tissue. The flow in such tissue is commonly impeded because of the pathological hydrophobic interactions between cells and/or certain molecules. The present invention includes the use of a surface active copolymer for treatment of diseases and conditions in which resistance to blood flow is caused by injury due to the presence of adhesive proteins or damaged membranes. Such proteins and damaged membranes increase resistance in the microvasculature by increasing friction and reducing the effective radius of the blood vessel. The most important of these proteins are fibrinogen and soluble fibrin.

The method comprises administering to an animal or human an effective amount of a surface active copolymer with the following general formula:

wherein a is an integer such that the hydrophobe represented by ($C_3H_6O$) has a molecular weight of approximately 950 to 4000, preferably about 1200 to 3500, and b is an integer such that the hydrophile portion represented by ($C_2H_4O$) constitutes approximately 50% to 95% by weight of the compound.

Also in accordance with the present invention, a fibrinolytic composition and method is provided that is effective in dissolving blood clots and reestablishing and maintaining blood flow through thrombosed coronary or other blood vessels. The fibrinolytic composition of the present invention comprises an enzyme, such as streptokinase, urokinase, prourokinase, tissue plasminogen activator, or other proteolytic enzyme, and a surface active copolymer. The surface active copolymer can be an ethylene oxide-propylene oxide condensation product with the following general formula:

wherein a is an integer such that the hydrophobe represented by ($C_3H_6O$) has a molecular weight of approximately 950 to 4000, preferably about 1200 to 3500, and b is an integer such that the hydrophile portion represented by ($C_2H_4O$) constitutes approximately 50% to 95% by weight of the compound.

The fibrinolytic composition of the present invention is usually administered by intravenous injection into a patient but can be administered by intramuscular or other parenteral injection.

The present invention provides a composition that can be administered to patients who have a blood clot occluding a blood vessel. The combination of proteolytic enzyme and surface active copolymer according to the present invention increases blood flow around a clot, rapidly lyses a clot, and provides futher protection to the patient by preventing a new clot from forming and reducing reperfusion injury.

Because the fibrinolytic composition of the present invention stabilizes the patient to a greater extent than treatments in the prior art, the administration of more invasive procedures, such as balloon angioplasty, can be delayed thereby permitting selection of conditions for the invasive treatment that are most favorable to the patient. In addition, the treatment of myocardial infarction by use of a proteolytic enzyme such as t-PA or streptokinase can be delayed because the addition of the surface active copolymer will limit the damage to the heart tissue.

Another embodiment of the present invention is a composition comprising the combination of the surface active copolymer and free radical scavengers including but not limited to, superoxide dismutase and mannitol, mercaptopropionyl glycine. The surface active copolymer can also be used with agents that prevent the generation of free radical species including, but not limited to, ibuprofen, BW755C, nafazatrom, prostacyclin, iloprost, allopurinol, phenytoin as well as other anti-inflammatory or cytoprotective drugs. It is to be understood that the term free radical scavengers includes both the scavenger compounds and the compounds that prevent the generation of free radial species. The present invention includes a composition comprising the combination of surface active copolymer, clot lysing enzyme and free radical scavenger and also the a composition comprising combination of surface active copolymer and free radical scavenger alone.

In accordance with the present invention, a composition and method is provided that is effective in prolonging the function and lifespan of platelets in suspension. The method comprises adding an effective amount of a surface active copolymer to the platelet suspension. The surface active copolymer can be an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, perferably about 1200 to 3500, and b is an integer such that the hydrophile portion represented by $(C_2H_4O)$ constitutes approximately 50% to 95% by weight of the compound.

The present invention also embodies a method for efficiently delivering drugs to and into diseased or damaged tissue. This includes tissue damaged by infection, trauma, burns, or other noxious insult.

Accordingly, it is an object of the present invention to provide a method of treating pathologic hydrophobic interactions of components in blood or other biological fluids.

It is a further object of the present invention to provide a method for protecting cells during and after an ischemic period.

It is a further object of the present invention to provide a method and composition for protecting tissue after a burn.

It is yet another object of the present invention to provide a method for protecting myocardial cells, endothelial cells and other cells from ischemia.

It is another object of the present invention to provide a method of enhancing the ability of cells and tissue to recover from ischemia.

It is an object of the present invention to provide a combination of fibrinolytic enzymes with a surface active copolymer to produce a synergistic action in lysing blood clots. This combination can be formulated either with standard doses of enzyme to increase the rate or likelihood of lysing a clot or at lower doses of enzyme to reduce side effects while maintaining efficacy for lysing clots.

It is another object of the present invention to provide a composition that will reduce the need for anticoagulation in therapy of thrombosis and thereby lessen the danger of hemorrhage.

It is another object of the present invention to provide a composition that accelerates the dissolution of clots by freeing aggregated platelets and blocking further platelets from aggregating to the clot.

It is yet another object of the present invention to provide a composition that can reduce the dose of proteolytic enzyme required to lyse a clot and thereby reduce the incidence of complications.

It is another object of the present invention to provide a composition that contains a surface active copolymer and a free radical or oxygen scavenger, such as superoxide dismutase mannitol, and/or mercaptopropionyl glycine.

It is a further object of the present invention to provide a composition that can promote blood flow through microvascular channels of tissue damaged by ischemia and reduce the amount of tissue which undergoes necrosis.

It is a further object of the present invention to provide a method for delivering drugs to damaged or diseased tissue.

It is a further object of the present invention to provide a composition that will significantly reduce the risk of rethrombosis after treatement with fibrinolytic enzymes.

If is a further object of the present invention to provide a composition that will promote removal of lipids from atherosclerotic vessel walls and thereby lessen the incidence of rethrombosis.

It is another object of the present invention to provide an improved fibrinolytic composition that is capable of lysing fibrin deposits associated with tumors.

It is another object of the present invention to provide a composition which will increase blood flow through tortuous channels such as occur in tumors and during crisis of sickle cell disease.

It is another object of the present invention to provide an improved composition and method for ex vivo preservation of organs.

It is another object of the present invention to provide a composition that will reduce the risk of rethrombosis and thereby allow delay in administering balloon angioplasty or other invasive procedures for treatment of the compromised vessels.

It is another object of the present invention to provide a composition which will reduce the risk of thrombosis immediately or at some time after invasive proce-

dures such as balloon angioplasty which damage endothelial cells of the vasculature.

It is a further object of the present invention to provide a composition to block the aggregation of platelets in blood vessels distal to the thrombosis and thereby limit extension of tissue damage.

It is yet another object of the present invention to provide a composition to improve blood flow through and around tissue with extensive necrosis of myocardial or other cells thereby retarding necrosis of additional myocardial tissue.

It is another object of the present invention to provide a composition which will reduce the influx of neutrophils into damaged tissue and thereby reduce the extent of injury caused by toxic products of neutrophils.

It is yet another object of the present invention to provide a composition that will decrease the amount of ischemia caused blockage of blood flow by a thrombus.

It is yet another object of the present invention to provide a method for increasing blood flow in ischemic or damaged tissue thereby reducing damage to the tissue.

It is another object of the present invention to provide a method for treating burns.

It is a further object of the present invention to provide a combination of a thrombolytic enzyme, balloon angioplasty or other operative procedures and a surface active copolymer to produce an improved method of removing a thrombus or thrombogenic occlusion and reducing obstructive conditions which promote rethrombosis.

It is another object of the present invention to provide a composition and method for the treatment of crisis in sickle cell disease.

It is another object of the present invention to provide a composition that is effective in restarting blood flow through microcapillaries after ischemia.

It is an object of the present invention to provide composition and method for prolonging the life-span and function of platelets.

It is another object of the present invention to provide a composition and method that will allow platelet suspensions to be stored for longer periods of time then is presently possible with prior art methods.

It is another object of the present invention to provide a composition and method that can be added to conventional platelet containers so that platelet suspensions can be stored for a longer period of time.

It is yet another object of the present invention to provide a composition and method that can be used to prolong the lifespan of cell suspensions.

It is yet another object of the present invention to provide a method of storing a concentrated suspensions of platelets whereby platelet function is prolonged thereby allowing longer storage times.

It is another object of the present invention to provide a method of storing a concentrated suspension of platelets for transfusion into a patient.

It is yet another object of the present invention to provide a composition and method for treatment of shock using a surface active copolymer with a plasma extender.

It is another object of the present invention to provide a method and composition for treating microvascular diseases caused by endotoxin such as endotoxin shock or laminitis in horses.

These and other objects, features and advantages of the present invention will become apparent after a review of the following detailed description of the disclosed embodiments and the appended claims.

DETAILED DESCRIPTION OF THE DISCLOSED EMBODIMENTS

Figure 1:
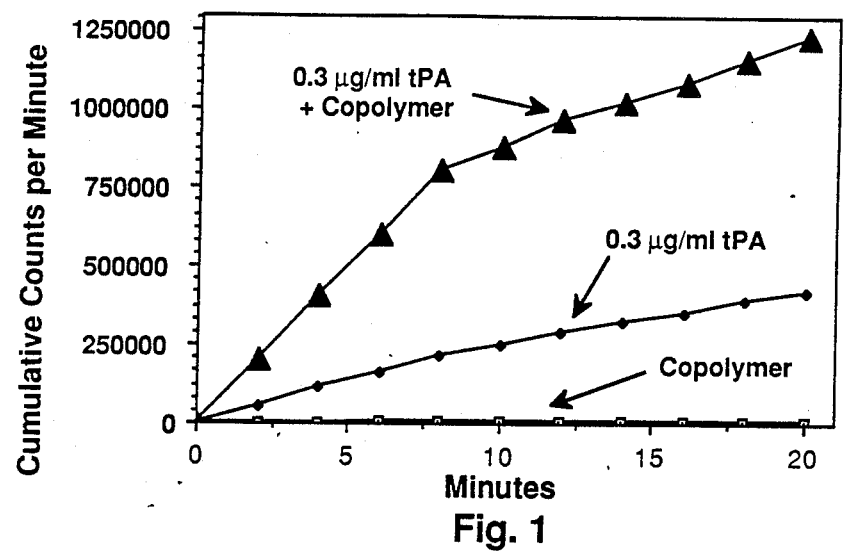
FIG. 1 is a graph showing the effect of the surface active copolymer on dissolving a clot with and without tPA.

In accordance with the present invention, a method is provided for treating pathologic hydrophobic interactions in blood and other biological fluids of humans and animals. The present invention includes the use of a surface active copolymer for treatment of diseases and conditions in which resistance to blood flow is pathologically increased by injury due to the presence of adhesive hydrophobic proteins or damaged membranes. This adhesion is produced by pathological hydrophobic interactions and does not require the interaction of specific ligands with their receptors. Such proteins and/or damaged membranes increase resistance in the microvasculature by increasing friction and reducing the effective radius of the blood vessel. It is believed that the most important of these proteins is soluble fibrin.

The method according to the present invention comprises administering to the animal or human suffering from a condition caused by a pathological hydrophobic interaction an effective amount of a surface active copolymer. The surface active copolymer may be administered as a solution by itself or it may be administered with another agent, including but not limited to, a fibrinolytic enzyme, an anticoagulant, or an oxygen radical scavenger.

The surface active copolymer in all embodiments of the present invention comprises the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably about 1200 to 3500, and b is an integer such that the hydrophile portion represented by $(C_2H_4O)$ constitutes approximately 50% to 95%, by weight of the compound.

The most preferred surface active copolymer for use in the method of the present invention is a copolymer having the following formula:

$$HO(C_2H_4O)_b(C_3H_6O)_a(C_2H_4O)_BH$$

wherein the molecular weight of the hydrophobe ($C_3H_6O$) is approximately 1750 and the total molecular weight of the compound is approximately 8400.

The surface active copolymer of the present invention is effective in any condition where there is a pathological hydrophobic interaction between cells and/or molecules. These interactions are believed to be caused by (1) a higher than normal concentration of fibrinogen, (2) generation of intravascular or local soluble fibrin, especially high molecular weight fibrin, (3) increased friction in the microvasculature, or (4) mechanical or chemical trauma to blood components. All of these conditions cause an increase in pathological hydrophobic interactions of blood components such as cells and molecules.

It is believed that fibrin, especially soluble fibrin, increases adhesion of cells to one another, markedly icnreases friction in small blood vessels and increases viscosity of the blood, especially at low shear rates. The effects of the surface active copolymer of the present invention are believed to be essentially lubrication effects because they reduce the friction caused by the adhesion.

Although not wanting to be bound by the following hypothesis, it is believed that the present invention acts according to the following mechanism: Hydrophobic interactions are crucial deteminants of biologic structure. They hold the phospholipids together in membranes and protein molecules in their native configurations. An understanding of the biology of the surface active copolymer is necessary to appreciate the biologic activities of the compound. Water is a strongly hydrogen bonding liquid which, in its fluid state, forms bonds in all directions with surrounding molecules. Exposure of a hydrophobic surface, defined as any surface which forms insufficient bonds with water, produces a surface tenhsion or lack of balance in the hydrogen bonding of water molecules.

This force can be exceedingly strong. The surface tension of pure water is approximately 82 dynes/cm. This translates into a force of several hundred thousand pounds per square inch on the surface molecules.

As two molecules or particles with hydrophobic surfaces approach, they adhere avidly. This adhesion is driven by the reduction in free energy which occurs when water molecules transfer from the stressed non-hydrogen bonding hydrophobic surface to the non-stressed bulk liquid phase.

The energy holding such surfaces together, the work of adhesion, is a direct function of the surface tension of the particles (See: Adamson AW *Physical Chemistry of Surfaces*, Fourth Edition, John Wiley & Sons, New York, 1982):

$$W_{AB} = \gamma A + \gamma B - \gamma AB$$

where $W_{AB}$ = work of adhesion or the energy necessary to separate one square centimeter of particle interface AB into two separate particles $\gamma A$ and $\gamma B$ are the surface tensions of particle A and particle B, $\gamma AB$ the interfacial tension between them.

Consequently, any particles or molecules in the circulation which develop significant surface tensions will adhere to one another spontaneously. Such adhesion within membranes and macromolecules is necessary to maintain their integrity. We use the term "normal hydrophobic interaction" to describe such forces. Under normal circumstances, all cells and molecules in the circulation have hydrophilic non-adhesive surfaces.

Receptors and ligands which modulate cell and molecular interactions are generally located on the most hydrophilic exposed surfaces of cells and molecules where they are free to move about in the aqueous media and to interact with one another. Special carrier molecules are necessary to transport lipids and other hydrophobic substances in the circulation. In body fluids such as blood, nonspecific adhesive forces between mobile elements are extremely undesirable. We term these "pathologic hydrophobic interactions" because they restrict movement of normally mobile elements and promote inappropriate adhesion of cells and molecules.

In damaged tissue, hydrophobic domains normally located on the interior of cells and molecules may become exposed and produce pathologic adhesive surfaces whose interaction compounds the damage. Fibrin deposited along vessel walls also provide an adhesive surface. Such adhesive surfaces appear to be characteristic of damaged tissue. It is believed that the ability of the surface active copolymer to bind to adhesive hydrophobic surfaces and convert them to non-adhesive hydrated surfaces closely resembling those of normal tissues underlies its potential therapeutic activities in diverse disease conditions.

Adhesion due to surface tension described above is different from the adhesion commonly studied in biology. The commonly studied adhesion is due to specific receptor ligand interactions. In particular, it is different from the receptormediated adhesion of the fibrinogen—von Willibrands factor family of proteins (See generally *Hemostasis and Thrombosis, Basis Principles and Clinical Practice*, ed. by Colman, et al., J.B. Lippincott Company (1987)).

Both the hydrophilic and hydrophobic chains of the surface active copolymer have unique properties which contribute to biologic activity. The hydrophilic chains of POE are longer than those of most surfactants and they are flexible. They bind water avidly by hydrogen bond acceptor interactions with ether-linked oxygens. These long, strongly hydrated flexible chains are relatively incompressible and form a barrier to hydrophobic surfaces approaching one another. The hydroxyl moieties at the ends of the molecule are the only groups capable of serving as hydrogen bond donors. There are no charged groups.

This extremely limited repertoire of binding capabilities probably explains the inability of the molecule to activate host mediator and inflammatory mechanisms. The POE chains are not necessarily inert, however. Polyoxyethylene can bind cations by ion-dipole interactions with oxygen groups. The crown polyethers and reverse octablock copolymer ionophores are examples of such cation binding (See Atkinson, TP, et al., Ion transport mediated by copolymers composed of polyoxyethylene and polyoxypropylene. *Am J Physiol* 254;C20, 1988). It is possible that the flexible POE chains form configurations which bind and modulate calcium and other cation movements in the vicinity of damaged membranes or othe hydrophobic structures.

The hydrophobic component of the surface active copolymer is large, weak and flexible. The energy with which it binds to a cell membrane or protein molecule is less than the energy which holds the membrane phospholipids together or maintains the tertiary conformation of the protein. Consequently, unlike common detergents which dissolve membrane lipids and proteins, the surface active copolymer adheres to damaged spots on membranes and prevents propagation of the injury.

The ability of the surface active copolymer to block adhesion of fibrinogen to hydrophobic surfaces and the subsequent adhesion of platelets and red blood cells is readily demonstrated in vitro. Most surfactants prevent adhesion of hydrophobic particles to one another, however, the surface active copolymer has a unique balance of properties which optimize the anti-adhesive activity while minimizing toxicity. Thus, the surface active copolymer is not routinely used by biochemists who use nonionic surfactants to lyse cells or dissolve membrane proteins. The surface active copolymer protects cells from lysis. The hydrophobe effectively completes with damaged cells and molecules to prevent pathologic hydrophobic interactions, but cannot disrupt the much stronger normal hydrophobic interactions which maintain structural integrity.

The viscosity of blood is generally assumed to be the dominant determinant of flow through vessels with a constant pressure and geometry. In the smallest vessels, however, those in damaged tissue, other factors become significant. When the diameter of the vessel is less than that of the cell, the blood cell must deform in order to enter the vessel and then must slide along the vessel wall producing friction. The deformability of blood cells entering small vessels has been extensively studied (See: Brooks DE and Evans EA Rheology of blood cells, in *Clinical Hemorheology. Applications in Cardiovascular and Hematological Disease, Diabetes, Surgery and Gynecology*. S Chien, J Dormandy, E Ernst, and A Matrai, eds, Martinus Nijhoff Publishers, Dordrecht, 1987), but the adhesive or frictional component has not. The adhesion of cells to vessel walls is generally attributed to specific interactions with von Willebrand's factor and other specific adhesive molecules (See: Thompson AR and Harker LA *Manual of Hemostasis and Thrombosis*, Edition 3, F A Davis Company, Philadelphia, 1983). Our data suggests that in pathologic situations, friction resulting from nonspecific physicochemical adhesion between the cell and the vessel wall becomes a major determinant of flow.

Mathematically, both the strength of adhesion between two particles and the friction force which resists sliding of one along the other are direct functions of their surface tensions which are largely determined by their degree of hydrophobic interaction. The friction of a cell sliding through a small vessel consists of an adhesion component and a deformation component (Lee LH Effect of surface energetics on polymer friction and wear, in *Advances in Polymer Friction and Wear*, Polymer Science and Technology, volume 5A. L. H Lee, editor, Plenum Press, New York, 1974) which are in practice difficult to separate:

$$F = F_a + F_d$$

where F is the friction of cells, Fa is the adhesion component and Fd is the deformation component.

The deformation component within a vessel differs from that required for entry into the vessel. It may be similar to that which occurs in larger vessels with blood flowing at a high rate of shear (Brooks and Evans, 1987). Friction within blood vessels has been studied very little, but undoubtedly involves the same principles which apply to polymer systems in which the friction force correlates directly with the work of adhesion (Lee, 1974):

$$F_a = kWA + c$$

where Fa is the adhesional component of the friction force, WA the work of adhesion, and k and c constants which pertain to the particular system studied. Many lubricants act as thin films which separate the two surfaces and reduce adhesion (See: Adamson, 1982).

The effect of the surface active copolymer on microvascular blood flow were evaluated in several models ranging from artificial in vitro systems where critical variables could be rigidly controlled to in vivo systems mimicking human disease. First, the surface active copolymer can be an effective lubricant when used at therapeutic concentrations in a model designed to simulate movement of large cells through small vessels. It markedly reduced the adhesive component of friction, but had no detectable effect on the deformation component of friction. Second, the surface active copolymer greatly accelerates the flow through the narrow channels formed by the thrombogenic surfaces of glass and air. A drop of blood was placed on a cover slip and viewed under a microscope with cinemicroscopy during the time it took the blood to flow to the edges of the cover slip in response to gentle pressure. The surface active copolymer inhibited the adhesion of platelets to the glass and maintained the flexibility of red cells which enabled them to pass through the microscopic channels. While the surface active copolymer did not inhibit the formation of rouleaux by red cells, it did cause the rouleaux to be more flexible and more easily disrupted. Third, the surface active copolymer increases the flow of blood through tortuous capillary-sized fibrin-lined channels by over 20-fold (See Example IX herein). It decreased viscosity of the blood by an amount (10%) far too small to account for the increased flow.

In a more physiologic model, the surface active copolymer increased coronary blood flow by a similar amount in isolated rat hearts perfused with human red blood cells at a 30% hematocrit following ischemic damage (See Example X herein).

In an in vivo model of stroke produced by ligature of the middle cerebral artery of rabbits, the surface active copolymer increases blood flow to ischemic brain tissue. As much as two-fold increase was measured by a hydrogen washout technique. In each of these models, there were controls for hemodilution and there was no measurable effect on viscosity at any shear rate measured.

It is believed that available data suggests that the surface active copolymer acts as a lubricant to increase blood flow through damaged tissues. It blocks adhesion of hydrophobic surfaces to one another and thereby reduces friction and increases flow. This hypothesis is strengthened by the observation that the surface active copolymer has little effect on blood flow in normal tissues where such frictional forces are small (See: Grover FL, Kahn RS, Heron MV, and Paton BC, A nonionic surfactant and blood viscosity. *Arch Surg* 106:307, 1973.)

The surface active copolymers of the present invention are not metabolized by the body and are quickly eliminated from the blood. The half-life of the copolymer in the blood is believed to be approximately two hours. It is to be understood that the surface active copolymer in the improved fibrinolytic composition of the present invention is not covalently bound to any of the other components in the composition nor is it covalently bound to any proteins.

The surface active copolymer can be administered with a fibrinolytic enzyme, a free radical scavenger, or it can be administered alone for treatment of certain circulatory conditions which either are caused by or cause pathological hydrophobic interactions of blood components. These conditions include, but not limited to, myocardial infarction, stroke, bowel or other tissue infarctions, malignancies, adult respiratory distress syndrome (ARDS), disseminated intravascular coagulation (DIC), diabetes, unstable angina pectoris, hemolytic uremic syndrome, red cell fragmentation syndrome, heat stroke, retained fetus, eclampsia, malignant hypertension, burns, crush injuries, fractures, trauma producing shock, major surgery, sepsis, bacterial, parasitic, viral and rickettsial infections which promote activation of the coagulation system, central nervous system trauma, and during and immediately after any major surgery. It is believed that treatment of the pathological hydrophobic interactions in the blood that occurs in these conditions significantly reduces microvascular and other complications that are commonly observed.

The surface active copolymer of the present invention is also effective in increasing the collateral circulation to undamaged tissues with compromised blood supply. Such tissues are frequently adjacent to areas of vascular occlusion. The mechanism appears to be reducing pathological hydrophobic interactions in small blood vessels. Circulatory conditions where the surface active copolymers are effective include, but are not limited to, cerebral thrombosis, cerebral embolus, myocardial infarction, unstable angina pectoris, transient cerebral ischemic attacks, intermittent claudication of the legs, plastic and reconstructive surgery, balloon angioplasty, peripheral vascular surgery, orthopedic surgery, especially when using a tourniquet.

The surface active copolymer has little effect on the viscosity of normal blood at shear rates ranging from 2.3 sec$^{-1}$ (low) to 90 sec$^{-1}$ (high). However, it markedly reduces the abnormally high viscosity found in postoperative patients and in those with certain pathologic conditions. This observation posed two questions: (1) what caused the elevated whole blood viscosity in these patients and, (2) what mechanisms did the surface active copolymer, which has only minor effects on the blood viscosity of healthy persons, normalize pathologic elevations in viscosity?

It is generally accepted that hematocrit and plasma fibrinogen levels are the major determinants of whole blood vicosity. This has been confirmed in normal individuals and in many patients with inflammatory conditions. However, these factors could not explain the changes that were observed. In patients having coronary artery cardiac bypass surgery, it was found that hematocrit fell an average of $23\pm4\%$ and fibrinogen fell $48\pm9\%$ within six hours after surgery. The viscosity did not decrease as expected, but increased from a mean of $23\pm2$ to $38\pm4$ centipoise (at a shear rate of 2.3 sec$^{-1}$). Viscosities in excess of 100 were found in some patients. The abnormally high viscosity of blood was associated with circulating high molecular weight polymers of soluble fibrin (See: Papadea C and Hunter R Effect of RheothRx TM copolymer on blood viscosity related to fibrin(ogen) concentration. *FASEB J* 2:A384, 1988). The soluble fibrin levels rose from $19\pm5$ μg/ml to $43\pm6$ μg/ml during surgery. These studies utilized a colorimetric enzymatic assay for soluble fibrin (Wiman, B. and Rånby, M., Determination of soluble fibrin in plasma by a rapid and quantitative spectrophotometric assay. *Thromb. Haemost* 55:189, 1986) and Western blotting procedures with SDS agarose gels to determine the molecular weight of the large protein polymers (See: Connaghan DG, Francis CW, Lane DA, and Marder VJ Specific identification of fibrin polymers, fibrinogen degradation products, and crosslinked fibrin degradation products in plasma and serum with a new sensitive technique. *Blood* 65:589, 1985).

In the absence of specific receptors, cells and molecules in the circulation adhere to one another if the adherence reduces the free energy or surface tension between them. An assessment of the surface tension of various components of the blood can be made by measuring contact angles.

Red blood cells, lymphocytes, platelets, neutrophils all have contact angles in the range of 14 to 17 degrees. Peripheral blood proteins, such as albumin, $\alpha_2$macroglobulin, and Hageman factor have contact angles in the slightly lower range of 12–15. This means that these proteins have no adhesive energy for the cells. In contrast, fibrinogen has a contact angle of 24 degrees and soluble fibrin of 31. Consequently, fibrinogen adheres weakly to red blood cells and other cells in the circulation promoting rouleaux formation. Fibrin promotes a very much stronger adhesion than fibrinogen because its elevated contact angle and its tendency to form polymers with fibrinogen. Soluble fibrin in the circulation produces the increased adhesion which results in a very markedly increased viscosity at low shear rates. This adhesion also involves the endothelial walls of the blood vessels. If the adhesive forces are insufficient to slow movement of cells, they produce an increased friction. This is especially important in the very small blood vessels and capillaries whose diameters are equal to or less than that of the circulating cells. The friction of cells sliding through these small vessels is significant. The surface active copolymer of the present invention blocks the adhesion of fibrinogen and fibrin to hydrophobic surfaces of cells and endothelial cells. This prevents their adhesion and lubricates them so there is a greatly reduced resistance to flow. This can be measured only partially by measurements of viscosity.

Whether a certain fibrinogen level is sufficient to cause a problem in circulation is dependent upon several parameters of the individual patient. High hematocrits and high levels of fibrinogen are widely regarded as the primary contributors to increased viscosity. However, elevated fibrinogen levels are frequently associated with elevated soluble fibrin in the circulation. Careful studies have demonstrated that the fibrin is frequently responsible for the most severe changes. The normal level of fibrinogen is 200–400 μg/ml. It has been determined that, in most patients, fibrinogen levels of greater than approximately 800 μg/ml will cause the high blood viscosity at the low shear rates mentioned hereinabove. The normal level of soluble fibrin has been reported to be approximately $9.2\pm1.9$ (Wiman, B. and Rånby, M., Determination of soluble fibrin in plasma by a rapid and quantitative spectrophotometric assay. *Thromb. Haemost* 55:189, 1986). Using the Wiman and Rånby assay, viscosity at low shear rates was unacceptably high above about 15 μg/ml. It must be understood that soluble fibrin means molecular species that have a molecular weight of from about 600,000 to several million.

Numerous methods have been used for demonstrating soluble fibrin. These include cryoprecipitation especially cryofibrinogen. Heparin has been used to augment the precipitate formation. Ethanol and protamine also precipitate fribrin from plasma. Modern techniques have demonstrated that the soluble fibrin in the circulation is generally complexed with solubilizing agents. These are most frequently fibrinogen or fibrin degradation products. Des AA fibrin in which only the fibrin of peptide A moieties have been cleaved, tends to form relatively small aggregates consisting of one molecule of fibrin with two of fibrinogen. If both the A and B peptides have been cleaved to produce des AABB fibrin, then much larger aggregates are produced in the circulation. Fibrin degradation products can polymerize with fibrin to produce varying size aggregates depending upon the particular product involved.

Soluble fibrin in the circulation can markedly increase blood viscosity, especially at low shear rates. However, the relevance of this for clinical situations remains unclear. Viscosity assesses primarily the aggregation of red blood cells which is only one of many factors which determine in vivo circulation. Other factors affected by soluble fibrin are the endothelial cells, white blood cells and platelets. Soluble fibrin is chemotactic for endothelial cells, adheres to them avidly and causes their disorganization. It also has stimulatory effects for white blood cells especially macrophages. Some of the effects of soluble fibrin may be mediated by specific receptors on various types of cells. However, since the free energy, as measured by contact angles of soluble fibrin, is less than that of any other plasma protein, it adheres avidly by a nonspecific hydrophobic interactions to virtually all formed elements in the blood.

Circulating soluble fibrin is normally cleared by macrophages and fibrinolytic mechanisms without producing damage. However, if the production of soluble fibrin is too great or if the clearance mechanism have been compromised or if complicating disease factors are present, then soluble fibrin can induce deleterious reactions.

Soluble fibrin is produced in damaged or inflamed tissues. Consequently, its effects are most pronounced in these tissues where it coats endothelial cells and circulating blood cells in a fashion which markedly reduces perfusion. The largest effects are in the small blood vessels where soluble fibrin coating the endothelial cells and white blood cells produces a severe increase in friction to the movement of white cells through the small vessels. Friction appears to be a much more severe problem with white blood cells and red blood cells because they are larger and much more rigid.

If production of soluble fibrin is sufficient, then effects are noticed in other areas. The best studied is the adult respiratory distress syndrome where soluble fibrin produced in areas of damaged tissue produces microthrombi and other processes in the lungs which can cause pulmonary failure. However, lesser degrees of vascular compromise can be demonstrated in many other organs.

Soluble fibrin, either alone or in complex with fibrinogen and other materials is now recognized as being a major contributor to the pathogenesis of a diverse range of vascular diseases ranging from coronary thrombosis through trauma, burns, reperfusion injury following transplantation or any other condition where there has been localized or generalized activation of coagulation.

A recent study demonstrated that virtually all patients with acute myocardial infarction or unstable angina pectoris have markedly elevated levels of soluble fibrin in their circulation.

An example of the effects of soluble fibrin has been shown in the studies using dogs. A normal dog is subjected to a hysterectomy. Then, while the animal is still under anesthesia, the external jugular vein is carefully dissected. Alternatively, the vein may be occuled by gentle pressure with the fingers for seven minutes. It is examined by scanning electron microscopy for adhesion of fibrin, red blood cells and other formed elements.

One finds that very few cells adhere to the endothelia of veins from dogs which had not undergone hysterectomy, whether or not there had been stasis produced by seven minutes occlusion. Similarly, there was only a small increase in adhesion of red blood cells to the endothelium of the jugular vein in animals who had undergone hysterectomy. If, however, the animals had a hysterectomy in addition to mild seven minute occlusion of the veins, then there was a striking increase in adhesion of formed elements of blood to the endothelial surfaces in some cases producing frank mural thrombi. Both red blood cells and fibrin were visibly adherent to the endothelial surfaces. In addition, there was disruption of the normal endothelial architecture. All of the animals had elevated levels of soluble fibrin after the surgery. This model demonstrates the effects of soluble fibrin produced by relatively localized surgery to produce a greatly increased risk of deep vein thrombosis at a distant site.

The surface active copolymer of the present invention addresses the problems of fibrin and fibrinogen in the blood by inhibiting the adhesion of fibrin, fibrinogen, platelets, red blood cells and other detectable elements of the blood stream. It blocks the formation of a thrombus on a surface. The surface active copolymer of the present invention has no effect on the viscosity of water or plasma. However, it markedly increases the rate of flow of water and plasma in small segments through tubes. The presence of air interfaces at the end of the columns or air bubbles which provide a significant surface tension produce a friction along the walls of the tubes. The surface active copolymer of the present invention reduces this surface tension and the friction and improves flow. This is an example whereby the surface active copolymer of the present invention improves flow of fluid through tissues through a tube even though it has no effect on the viscosity of the fluid as usually measured.

The surface active copolymer of the present invention has only a small effect on the viscosity of whole blood from normal individuals. It has little effect on the increase that occurs within high hematocrit. However, it has an effect on the very large increase in viscosity at low shear rates thought to be caused by soluble fibrin and fibrinogen polymers.

Recent studies demonstrate that the surface active copolymer also has the ability to protect myocardial and other cells from a variety of noxious insults. During prolonged ischemia, myocardial cells undergo "irreversible injury." Cells which sustain irreversible injury are morphologically intact but are unable to survive when returned to a normal environment. Within minutes of reperfusion with oxygenated blood, cells containing such occult lesions develop swelling and contraction bands and die.

Irreversibly injured myocardial cells have mechanical and osmotic fragility and latent activation of lipases, proteases and other enzymes. Reperfusion initiates a series of events including calcium loading, cell swelling, mechanical membrane rupture and the formation of oxygen free radicals which rapidly destroy the cell. The surface active copolymer retards such injury in the isolated perfused rat heart model. The mechanisms probably include osmotic stabilization and increased mechanical resistance in a fashion similar to that known for red blood cells.

The protective effects of the surface active copolymer on the myocardium are not limited to the myocardial cells. It also protects the endothelial cells of the microvasculature as assessed morphologically. By maintaining the integrity of such cells and helping to restore and maintain non-adhesive surfaces, the surface active copolymer tends to reduce the adhesion of macromolecules and cells in the microvasculature, to reduce coronary vascular resistance and to retard development of the no reflow phenomenon.

Examples of conditions where the present invention can be used is in the treatment of sickle cell disease and preservation of organs for transplantation. In both of these embodiments, blood flow is reduced because of pathologic hydrophobic interactions.

During a sickle cell crisis, sickled red blood cells aggregate because of the abnormal shape of the cells. In many cases, there are high concentrations of soluble fibrin due to disseminated intravascular coagulation. This results pathological hydrophobic interactions between blood cells, cells lining the blood vessels and soluble fibrin and fibrinogen. By administering to the patient the surface active copolymer embodied in the present invention, blood flow is increased and tissue damage is thereby reduced. It is contemplated as part of the present invention that the surface active copolymer may be given prior to a sickle cell crisis to prevent onset of the crisis. In addition, the solution with the effective amount of surface active copolymer may also contain an effective amount of anticoagulant.

In organs that have been removed from a donor for transplantation, the tissue is damaged due to ischemia and lack of blood. Preferably, the surface active copolymer is mixed with a perfusion medium. The perfusion media that can be used with the surface active copolymer are well known to those of ordinary skill in the art. The perfusion media can also be whole blood or plasma. The solution can be perfused through the organ thereby reducing the damage to the tissue. Because the tissue damage is reduced by perfusing the organ with the surface active copolymer solution, the time the organ is viable and therefore the time the organ can be transplanted is increased.

Because the surface active copolymer improves flow of blood through diseased or damaged tissue with minimal effect on blood flow in normal tissue, it is contemplated that the present invention includes a method for delivering drugs to damaged tissue comprising the step of administering to the animal or human a solution containing:
an effective amount of a drug; and
an effective amount of a surface-active copolymer with the following general formula:

wherein a is an integer such that the hydrophobe represented by ($C_3H_6O$) has a molecular weight of approximately 950 to 4000, and b is an integer such that the hydrophile portion represented by ($C_2H_4O$) constitutes approximately 50% to 95% by weight of the compound.

Any drug that has an activity in diseased or damaged tissue is suitable for this embodiment of the present invention. These drugs include
1. Antimicrobial drugs
   antibiotics
   antifungal drugs
   antiviral drugs
   antiparasitic drugs
2. antifungal drugs;
3. chemotherapeutic drugs for treating cancers and certain infections;
4. free radical scavenger drugs including those drugs that prevent the production of free radicals;
5. fibrinolytic drugs;
6. perfusion media;
7. antiinflammatories, including but not limited to both steroids and nonsteriod antiinflammatory drugs
8. membrane stabilizers such as dilantin;
9. anticoagulants;
10. ionotropic drugs such as calcium channel blockers;
11. autonomic nervous system modulators;

Solutions which may be employed in practicing the present invention include, but are not limited to, saline (a solution of sodium chloride, containing approximately 8.5 to 9.5 grams of sodium chloride in 1000 cc of purified water), Ringer's solution, lactated Ringer's solution, Krebs-Ringer's solution, and various sugar solutions. All of these solutions are well known to one of ordinary skill in the art. Other isotonic solutions can be used to prepare a solution of the surface active copolymer. However, it is to be understood that the present invention may be administered as a solution that is not isotonic. The surface active copolymer can be administered in a non-aqueous solution.

The method for treating pathologic hydrophobic interactions of the present invention includes administering the solution of surface active copolymer by intravenous injection. However, it is to be understood that the solution of surface active copolymer can be administered by intramuscular, subcutaneous parenteral or any other route of injection. It is contemplated as part of the present invention that the surface active copolymer could be administered orally either with an agent that promotes absorption of the copolymer by the gastrointestinal tract or by the surface active copolymer itself. In addition, the surface active copolymer can be administered transdermally.

The final concentration of surface active copolymer in blood or other biologic fluids used to practice the present invention is between approximately 0.01 and 10 mg/ml. The preferred concentration of surface active copolymer used to practice the present invention is between approximately 0.1 and 2 mg/ml with the most preferred concentration between approximately 0.4 and 0.8 mg/ml of fluid.

The present invention also comprises a composition which lyses blood clots and reestablishes and maintains blood flow through a thrombosed coronary vessel or other blood vessel. The fibrinolytic composition of the present invention is a solution containing an effective concentration of a proteolytic enzyme and an effective concentration of a surface active copolymer. The combination of the two components is surprisingly effective in dissolving blood clots that are blocking blood vessels. In addition, the fibrinolytic composition of the present invention is highly effective in preventing a blood clot from reforming and in maintaining blood flow through the blood vessel and affected ischemic tissue.

The present invention also encompasses the combination of an effective amount of surface active copolymer and an effective amount of free radical scavenger including, but not limited to, superoxide dismutase (SOD), mannitol, or mercaptopropionyl glycine or a combination of two or more of the compounds. The combination of the two substances has been shown to increase the flow of blood through ischemic tissue. In particular, the combination of surface active copolymer and SOD or mannitol has been shown to increase tissue survival after occlusion of blood flow to the tissue (See Example VII and VIII herein).

It is thought that the fibrinolytic composition of the present invention improves the flow of blood through narrow passages around clots and thereby increases the delivery of the proteolytic enzyme to the clot. The present invention also speeds the rate of dissolution of the clot by the enzyme and increases the proportion of clots lysed by promoting delivery of enzyme to clots which would not otherwise be exposed to sufficient enzyme for their dissolution. In addition, the fibrinolytic composition of the present invention reduces the dose of fibrinolytic enzyme required for particular applications and thereby reduces the incidence of complications due to side effects caused by the enzymes.

The fibrinolytic composition of the present invention reduces the risk of immediate rethrombosis by accelerating the dissolution of clots and freeing aggregated platelets and blocking further platelets from aggregating to the clot or clot site. By reducing the risk of immediate rethrombosis, the fibrinolytic composition of the present invention will allow delay of balloon angioplasty or other invasive procedures for treatment of the compromised vessels which have become thrombosed. The delay will permit selection of conditions for invasive treatment most favorable to the patient.

Solutions which may be employed in the preparation of the fibrinolytic composition of the present invention include, but are not limited to, saline (a solution of sodium chloride, containing approximately 8.5 to 9.5 grams of sodium chloride in 1000 cc of purified water), Ringer's solution, lactated Ringer's solution, Krebs-Ringer's solution, and various sugar solutions. All of these solutions are well known to one of ordinary skill in the art. However, it is to be understood that the fibrinolytic composition of the present invention may be administered as a solution that is not isotonic.

The present invention includes use of the surface active copolymer with an effective amount of anticoagulant to permit blood flow through ischemic tissue. Anticoagulants that can be used with the present invention include, but are not limited to, heparin, low molecular weight heparin, coumarin derivatives, and warfarin. It is to be understood that the surface active copolymer of the present invention could be used with any one anticoagulant or with a combination of anticoagulants. It is also understood that the concentration of anticoagulant to be used with the surface active copolymer is well known to those of ordinary skill in the art. It has been found that administration of the surface active copolymer with anticoagulants increases blood flow through the ischemic tissue in a synergistic manner (See Example VI herein).

The surface active copolymer is preferably an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably from 1750 to 3500, and b is an integer such that the hydrophile portion represented by $(C_2H_4O)$ constitutes from about 50% to 95% by weight of the compound. These copolymers are sold under the general trademark of Pluronic ® polyols and are available from the BASF Corporation (Parsippany, N.J.). The preferred formula of the present invention is sold under the trademark RheothRx ® copolymer and is available from CytRx ® Corporation (Norcross, Ga.).

The present invention also includes A method for preventing blockage in catheters comprising adding an effective amount of a surface active copolymer to the fluid being delivered through the catheter, said surface active copolymer comprising the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, and b is an integer such that the hydrophile portion represented by $(C_2H_4O)$ constitutes approximately 50% to 95% by weight of the compound. It is contemplated that the surface active copolymer can be used to maintain the catheter over long periods of time. The method of the present invention can be used to maintain the patency of catheters and dialysis materials in hemodialysis, peritoneal dialysis, intravascular catheters, bladder catheters and central nervous catheters.

The preferred concentration of the surface active copolymer of the present invention for use in maintaining catheters and the like is between approximately 0.01 mg/ml and 10 mg/ml with a preferred concentration of between 0.1 mg/ml and 2 mg/ml. The method of the present invention blocks adhesion of proteins to catheters that are implanted intraperitoneally, intrapleurally or in any body cavity thereby reducing the potential for infection.

The present invention also provides a composition and method for storing concentrated platelet suspensions in a bag or other container. The present invention allows the platelet suspension to be stored either at room temperature or at refrigerator temperatures for longer periods of time than possible with prior art methods while still maintaining the platelets in a state where they are useful for transfusion into a patient. This state includes retention of platelet function and morphology.

Platelets suspensions treated according to the present invention can be stored in conventional plastic bags normally used to store platelets. Experiments with human platelet show that these platelet suspensions treated according to the present invention do not aggregate spontaneously as much as untreated platelets. Treated platelets retain their ability to aggregate in response to various stimuli such as adenosine diphosphate (ADP), thrombin, collagen, and epinephrine for a much longer time than untreated platelets.

The method of storing platelets according to the present invention includes adding an effective amount of a surface active copolymer to a suspension of platelets and mixing briefly to disperse the copolymer throughout the platelet suspension. Alternatively, the copolymer can be added to the platelet container before adding the platelet suspension. In this way, the containers can be supplied to the blood bank or other location where blood is processed and the platelet suspension can be added to the container with the copolymer. The container with the platelet suspension therein can then be stored until the platelets are to be used.

Prior art methods of storing platelet suspensions have been largely unsatisfactory. Platelet function, as measured by the ability of platelets to respond to aggregation stimuli, in platelet suspensions stored at room temperature is rapidly lost. When platelets are stored according to the present invention, platelets can be stored for longer period of time and retain platelet function. The preferred concentration of the surface active copolymer of the present invention for use in preserving platelets is between approximately 0.01 mg/ml and 10 mg/ml with a preferred concentration of between 0.1 mg/ml and 2 mg/ml.

Another embodiment of the present invention is an improved plasma extender composition and method of use. The improved plasma extender of the present invention comprises a conventional plasma extender and an effective amount of a surface active copolymer with the following general formula:

wherein a is an integer such that the hydrophobe represented by ($C_3H_6O$) has a molecular weight of approximately 950 to 4000, preferably from 1750 to 3500, and b is an integer such that the hydrophile portion represented by ($C_2H_4O$) constitutes from about 50% to 95% by weight of the compound.

The plasma extenders that can be used with the present invention include, but are not limited to, various dextran solutions, hydroxyethyl starch, and albumin and both natural and fixed or stabilized hemoglobin. The preferred concentration of the surface active copolymer of the present invention for use with plasma extenders is between approximately 0.01 mg/ml and 10 mg/ml with a preferred concentration of between 0.1 mg/ml and 2 mg/ml. The most preferred concentration of the surface active copolymer is approximately 0.6 mg/ml.

The concentration of surface active copolymer contemplated in the present invention can vary depending on the total volume of solution needed in the particular circumstances. The total amount of block copolymer employed in the present invention will also vary depending on the size and type of thrombus or embolus, the particular copolymer employed, the particular proteolytic enzyme employed, and the size and weight of the patient.

The copolymer can be used over a wide range of concentrations with no severe adverse side effects. It is believed that the copolymer is rapidly excreted intact; as much as 90% of the copolymer administered is excreted within three hours. Because of its low toxicity and the rapid clearance from the body, the copolymer can be administered over a long period of time.

The surface active copolymer of the present invention may be employed by admixing with blood in any standard manner. Preferably, however, the solutions are intravenously injected into the blood stream either as a bolus, slow drip or a combination of both. The solutions are generally admixed with the blood in a manner so as to maintain a substantially steady venous pressure.

It is to be understood that separate administration of a solution of the surface active copolymer and a fibrinolytic enzyme or other agent are contemplated in the present invention. For example, a solution of the surface active copolymer and a solution of a fibrinolytic enzyme could be prepared separately and administered simultaneously or sequentially to a patient suffering from a thrombus blocking a coronary artery. Simultaneous or sequential administration of the two components (copolymer and fibrinolytic enzyme) of the fibrinolytic composition of the present invention has the same effect as administering the components together and is therefore contemplated in the present invention.

The proteolytic enzymes that can be used in the fibrinolytic composition of the present invention include, but are not limited to, streptokinase (available from Hoechst-Roussel under the trademark Streptase ®), urokinase (available from Abbot Laboratories, North Chicago, Ill. under the trademark Abbokinase ®) and tissue plasminogen activator and Activase ™ (Genentech, South San Francisco, Calif.). The tissue plasminogen activator can be derived from eukaryotic cells such as human melanoma cells or can be made by genetic engineering methods. Some of the fibrinolytic enzymes are only sparingly soluble in water and must therefore be emulsified with the surface active copolymer before administration to the patient.

Ideally, a bolus injection of the copolymer solution without the enzyme is administered before the present invention is administered. For example, a 3% solution of the copolymer in 5% isotonic dextrose is injected within a two minute period so that the blood concentration of copolymer is approximately 0.6 mg/ml. In addition, it can be advantageous to administer a solution of the copolymer by intravenous drip at a rate of about 25 mg/kg body weight/hour to obtain of blood concentration of the copolymer of approximately 0.6 mg/ml for up to four days or longer following the administration of the fibrinolytic composition of the present invention. This treatment will aid in preventing a clot from reforming.

The surface active copolymer blocks are formed by condensation of ethylene oxide and propylene oxide at elevated temperature and pressure in the presence of a basic catalyst. There is some statistical variation in the number of monomer units which combine to form a polymer chain in each copolymer. The molecular weights given are approximations of the average weight of copolymer molecule in each preparation. It is to be understood that the blocks of propylene oxide and ethylene oxide do not have to be pure. Small amounts of other materials can be admixed so long as the overall physical chemical properties are not substantially changed. A more detailed discussion of the preparation of these products is found in U.S. Pat. No. 2,674,619 which is incorporated herein by reference.

Illustrative ethylene oxide-propylene oxide condensation products which may be employed in the preparation of the fibrinolytic composition of the present invention include, but are not limited to, the following copolymers:

1. A polyol with an average molecular weight of 4700 containing approximately 80% by weight ethylene oxide.
2. A polyol with an average molecular weight of 3400 containing approximately 50% by weight ethylene oxide.
3. A polyol with an average molecular weight of 7700 containing approximately 70% by weight ethylene oxide.
4. A polyol with an average molecular weight of 14,600 containing approximately 80% by weight ethylene oxide.
5. A polyol with an average molecular weight of 12,600 containing approximately 70% by weight ethylene oxide.
6. A polyol with an average molecular weight of 9500 containing approximately 90% by weight ethylene oxide.

The preferred ethylene oxide-propylene oxide copolymer for use in the fibrinolytic composition of the present invention is a copolymer having the following formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is approximately 8400.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

Addition of the copolymer to a clot dissolving enzyme results in a synergistic effect on the clot dissolving activity of the enzyme as demonstrated in this Example.

Sterile 1 ml tuberculin syringes are packed with 0.6 ml of 500 to 750 micron glass beads (Polyscience, Inc., Warington, Pa.). The tips of the syringes are plugged with nytex filters and a one-way plastic stopcock. Fresh frozen platelet-poor citrated plasma is spiked with 15 $\mu Ci/ml$ $^{125}I$ human fibrinogen (Sigma Chemical Co., St. Louis, Mo.). The radioactive plasma is diluted 1:2 with normal saline, and recalcified with calcium (American Dade, Aquada, Puerto Rico) at 1 volume of calcium to 4 volumes diluted plasma.

Radioactive fibrinogen is bound to the glass bead columns as follows: Equal volumes of the radioactivity labelled recalcified plasma are added to parallel bead columns and allowed to run through the beads with no excess plasma above the beads. All procedures and manipulations of the "bead clots" are performed at 37° C. The bead/plasma clots are allowed to incubated for 30 minutes, then washed for 30 minutes with normal saline. During the last 5 minutes of the wash with saline, the flow rates are monitored and columns whose flow rates are abnormally fast or slow are excluded form the experiment. Normal flow rates average 0.2 ml/minute.

The copolymer that is used in this example has the following formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is approximately 8400. The copolymer is prepared as a stock solution of 1% copolymer by weight in normal saline.

Blood containing t-PA, with or without the copolymer, is passed through the columns as follows: 10 ml of heparinized whole blood is drawn fresh and mixed with t-PA (10 $\mu g$ in 1 ml normal saline; single chain; Sigma Chemical Co. St. Louis, Mo.). A volume of 5.5 ml of blood is mixed with either 0.5 ml normal saline or 0.5 ml of copolymer stock solution. One aliquot of a preparation of whole blood or whole blood diluted 1:3 with normal saline is run on each column. Three ml of each blood preparation is added to a reservoir connected to each column. Fractions are collected every minute until all flow ceased. The volume in each tube is measured and radioactivity counted in a Tracor Analytic gamma counter (TmAnalytic, Inc., Elk Grove Village, Ill.) Appearance of radioactivity in the collection tubes indicates lysis of the clot.

The data are summarized in Table A and FIG. 1. FIG. 1 shows cumulative $^{125}I$ fibrinogen (counts per minute) released from the columns plotted as a function of time.

TABLE A

| Perfusate* | Time (Minutes) | Volume Recovered | Counts Minute (Volume) | Counts Minute (ml) | Counts Minute (Cumulative) |
|---|---|---|---|---|---|
| Blood, t-PA, Copolymer | 1 | 0.3 | 2031 | 6770 | 2031 |
| | 2 | 0.25 | 3042 | 12168 | 5073 |
| | 3 | 0.3 | 13051 | 43503 | 18124 |
| | 4 | 0.2 | 40190 | 200950 | 58314 |
| | 5 | 0.25 | 40260 | 161040 | 98574 |
| | 6 | 0.25 | 40009 | 160036 | 138583 |
| Blood, t-PA | 1 | 0.15 | 885 | 5900 | 885 |
| | 2 | 0.2 | 1330 | 6650 | 2215 |
| | 3 | 0.2 | 3681 | 18405 | 5896 |
| | 4 | 0.3 | 16333 | 54443 | 22229 |
| | 5 | 0.4 | 24932 | 62330 | 47161 |
| | 6 | 0.45 | 30545 | 67878 | 77706 |
| | 7 | 0.6 | 40365 | 67275 | 118071 |
| Blood, Copolymer | 2 | 0.8 | 340 | 425 | 340 |
| | 3 | 0.7 | 351 | 501 | 691 |
| | 4 | 0.6 | 270 | 450 | 961 |
| | 5 | 0.6 | 226 | 377 | 1187 |
| | 6 | 0.5 | 204 | 408 | 1391 |
| | 7 | 0.4 | 178 | 445 | 1569 |

A simulated thrombus containing $^{125}I$ fibrin was prepared as described in the text. The ability of test preparations to dissolve the fibrin was determined by measuring the rate of elution of radioactivity from the column. The copolymer is not an enzyme and has no reactive groups, so it is unable to lyse cross-linked fibrin, but it does increase the fibrinolytic activity of t-PA in this model which was designed to simulate the structure and flow conditions of a coronary thrombus.

As can be seen from Table A and FIG. 1, treatment of the radioactive clot with the surface active copolymer releases little of the radioactivity indicating no lysis of the clot. Administration of t-PA to the clot causes release of radioactivity indicating lysis of the clot in the column. However, when the surface active copolymer is added to the solution, the rate of lysis of the clot in the column is dramatically increased. Thus, the combination of surface active polymer and t-PA lysed the clot in the column at a significantly faster rate than did t-PA alone.

In other experiments, the model is modified by changing the size of the beads, the concentration of plasma used to make the clot, the dilution of blood or the concentration of enzyme or copolymer. In several instances, columns are produced in which whole blood fails to flow at all while blood with copolymer flows at a rate of about 0.05 ml/minute. t-PA in the blood is unable to dissolve any of the fibrin in such clots as measured by release of $^{125}I$ label because there is no flow of blood through the clot. The use of copolymer with the blood and t-PA in such situations caused rapid lysis of the clot.

EXAMPLE II

The fibrinolytic composition is tested in an ex vivo rat heart model. The detailed design of the system is described elsewhere. (See Paulson, et al., *Basic Res. Cardiol.*, Vol. 81, pp. 180–187, 1986). This model measures the ability of the isolated heart to recover from a 30 to 90 minute ischemic period where the flow of nutrients is reduced to 10 percent of normal or completely stopped, then followed by a 10 minute period of reperfusion. Three parameters measured: (1) cardiac output (CO); (2) left ventricular systolic pressure (LVSP); and (3) left ventricular contraction (dp/dt). Assessment of heart recovery and amount of damage are discussed in Paulson, D. J. et al. *Basic Res. Cardiol.*, Vol. 79, pp. 551–561, 1984.

In this experiment, hearts are perfused with washed whole human blood with no heparin added. Flow is completely stopped for 30 minutes, followed by 10 minutes reperfusion with washed whole human blood without heparin but with the additive or additives indicated in Table B. The copolymer that is used in this example has the following formula:

$$HO(C_2H_4O)_b(C_3H_6O)_a(C_2H_4O)_bH$$

wherein the molecular weight of the hydrophobe $(C_3H_6O)$ is approximately 1750 and the total molecular weight of the compound is approximately 8400. The copolymer is prepared as a stock solution of 1% copolymer by weight in normal saline.

The results of the test are as follows. The final concentration of the surface active copolymer used in this Example is 0.68 mg/ml. The streptokinase that is used in this Example is obtained from Sigma Chemical Company, St. Louis, Mo. Streptokinase is administered at a concentration of 100 units/heart.

The results are shown in Table B.

TABLE B

| Additions | Percent Cardiac Recovery (Values are mean) | | |
|---|---|---|---|
| | CO | LVSP | dp/dt |
| Whole Blood | 5 | 24 | 10 |
| with copolymer[1] | 38 | 82 | 65 |
| with streptokinase[2] | 33 | 75 | 60 |
| with copolymer and Streptokinase | 58[4] | 88 | 78 |
| With SOD[3] | 9 | 5 | 5 |
| with copolymer and SOD | 85[5] | 92 | 96 |
| with copolymer, SOD | 84[5] | 93 | 92 |

TABLE B-continued

| Additions | Percent Cardiac Recovery (Values are mean) | | |
|---|---|---|---|
| | CO | LVSP | dp/dt |
| and streptokinase | | | |

[1] The final concentration of copolymer is approximately 0.6 mg/ml.
[2] The amount of streptokinase is approximately 100 units/heart.
[3] The amount of SOD is 3000 units/heart.
[4] p < 0.5 for cardiac output (CO) differences between the group of the combination of (a) Copolymer and Streptokinase and (b) copolymer, streptokinase and SOD and the group of (a) whole blood ischemic control, (b) Copolymer only, and (c) Streptokinase only. Student's test was used to determine differences between independent means. A result of p < 0.5 was regarded as significant.
[5] Not done As can be seen from Table B, the copolymer and streptokinase combination protected the heart better than the copolymer or treptokinase alone. The combination of SOD and the surface active copolymer protected the heart muscle from the effects of blood deprivation better than the copolymer alone, SOD or the copolymer streptokinase combination when using cardiac output as a measure of heart muscle viability. In addition, coronary artery resistance showed improvement with the surface active copolymer present in the perfusion medium.

EXAMPLE III

For testing a patient weighing about 180 lbs with a pulmonary embolism, reconstitute 500 mg of urakinase (Abbokinase, Abbot Laboratories, North Chicago, IL.) in 105 ml of sterile water. To the urikinase solution add 90 ml of an 0.9% sodium chloride solution containing 6 grams of an ethylene oxide-propylene oxide copolymer with the following formula:

$$HO(C_2H_4O)_b(C_3H_6O)_a(C_2H_4O)_bH$$

wherein the molecular weight of the hydrophobe $(C_3H_6O)$ is approximately 1750 and the total molecular weight of the compound are thoroughly mixed to form a homogeneous solution. The final volume of the solution is 195 ml.

Administer the fibrinolytic composition of the present invention by means of a constant infusion pump that is capable of delivering a total volume of 195 ml. A priming dose of the fibrinolytic composition of the present invention is administered at a rate of 90 ml/hour over a period of 10 minutes. This is followed by a continuous infusion of the present invention at a rate of 15 ml· hour for 12 hours. Since some of the fibrinolytic composition of the present invention will remain in the tubing at the end of an infusion pump delivery cycle, the remaining solution is flushed out of the tube by administering a solution of 0.9% sodium chloride at a rate of 15 ml/hour.

EXAMPLE IV

For treating a patient with a coronary artery thrombi, reconstitute 75 mg of urokinase (Abbokinase, Abbot Laboratories, North Chicago IL.) in 15.6 ml of sterile water. To the urokinase solution add 300 ml of 5% dextrose solution containing 15 grams of an ethylene oxide-propylene oxide copolymer with the following general formula:

$$HO(C_2H_4O)_bC_3H_6O)_a(C_2H_4O)_bH$$

wherein the molecular weight of the hydrophobe $(C_3H_6O)$ is approximately 1750 and the total molecular weight of the compound is approximately 8400. The urokinase and the copolymer are thoroughly mixed to form a homogeneous solution. The solution is then diluted with 5% dextrose to a final volume of 500 ml.

The solution comprising the present invention is infused into the occluded artery at a rate of 4 ml per minute for periods up to 2 hours. To determine response to the solution of the fibrinolytic composition of the present invention, periodic angiography is performed.

EXAMPLE V

For treating a patient weighing about 180 lbs with a pulmonary embolism, reconstitute 500 mg of urokinase (Abbokinase, Abbot Laboratories, North Chicago, IL.) in 105 ml of sterile water. To the urokinase solution add 90 ml of an 0.9% sodium chloride solution containing 6.0 grams of an ethylene oxide-propylene oxide copolymer with the following general formula:

wherein the molecular weight of the hydrophobe ($C_3H_6O$) is approximately 1750 and the total molecular weight of the compound is approximately 8400. The urokinase and the copolymer are thoroughly mixed to form a homogeneous solution. The solution is then diluted with 0.9% sodium chloride to a final volume of 195 ml.

Administer 137 ml of a 5% isotonic dextrose solution with 3% wt/vol ethylene oxide-propylene oxide copolymer lysed therein to the patient over a 2 minute period. This gives a blood concentration of copolymer of approximately 0.6 mg/ml (assuming blood is 8% of body weight).

The fibrinolytic composition of the present invention is then immediately administered by means of a constant infusion pump that is capable of delivering a total volume of 195 ml. A priming dose of the present invention is administered at a rate of 90 ml/hour over a period of 10 minutes. This is followed by a continuous infusion of the present invention at a rate of 15 ml/hour for 12 hours. Since some of the present invention will remain in the tubing at the end of an infusion pump delivery cycle, the remaining solution is flushed out of the tube by administering a solution of 0.9% sodium chloride containing 3.0% copolymer at a rate of 15 ml/hour.

After the clot is lysed, a solution of the copolymer is administered by intravenous drip at a rate of about 25 mg/kg body weight/hour to maintain a blood concentration of the copolymer of approximately 0.6 mg/ml. The administration of the copolymer solution is continued for four days following the administration of the fibrinolytic composition of the present invention.

EXAMPLE VI

The effect of the surface active copolymer and an anticoagulant in tissue following ischemic damage is demonstrated in this example. The composition comprising the surface active copolymer and an anticoagulant, such as heparin, shows synergistic results. Reconstitute 1000 units of heparin (Sigma Chemical Company, St. Louis, MO.) in 200 ml of normal (0.9%) sodium chloride solution and add 1.36 g of the copolymer of the present invention and resuspend washed whole human blood to formulate the perfusion medium. The copolymer has the following general formulation:

wherein the molecular weight of the hydrophobe ($C_3H_6O$) is approximately 1750 and the total molecular weight of the compound is 8400.

Hearts excised from anesthetized Sprague-Dawley rats were perfused for 10 minutes with (a) blood and heparin or with (b) blood, heparin and copolymer following a 90 minute low-flow ischemia. Cardiac output (CO), left ventricular systolic pressure (LVSP) and left ventricular contraction (dp/dt) were determined and are expressed as percent of recovery as compared to normal hearts. Ischemic animals' hearts which received blood with heparin showed poor recovery: 12% CO, 44% LVSP and 34% dp/dt. Hearts given blood, heparin and copolymer showed excellent recovery: 90% CO, 92% LVSP, and 84% dp/dt. For the heparin with Copolymer group, all three parameters were statistically different ($p<0.01$) as compared to the ischemic control group (heparin only). Differences between independent means were determined by the Student's test. This example also illustrates the ability of the copolymer to improve flow through damaged tissue by virtue of its lubricating properties under conditions where there is not thrombus or embolus formation.

EXAMPLE VII

A test is performed to demonstrate the ability of the combination of superoxide dismutase (SOD) and an appropriate copolymer to produce greater protection of ischemic myocardium from reperfusion injury associated with oxygen radicals and other factors than SOD alone.

Under general anesthesia (sodium thiopental 25 mg/kg), the dogs are intubated and ventilated with 70% oxygen at a rate of 12 breaths per minute. A satisfactory level of anesthesia is maintained with intermittent boluses of pentothal as required. After skin preparation, a left anterior thoracotomy is performed, the pericardium incised and the heart exposed. The left anterior descending (LAD) coronary artery is identified, isolated and encircled with a snare 1 cm from its origin. Temporary LAD occlusion is accomplished by tightening the snare and continues for 90 minutes. During the procedure, the heart rate and blood pressure are monitored utilizing a Hewlett-Packard 7758B 8-channel recorder. Arterial blood pressure is monitored through an 18 gauge indwelling catheter in the right femoral artery and measured with a Hewlett-Packard quartz transducer. Electrocardiographic evidence for anteroseptal myocardial ischemia is also monitored. Reperfusion of the ligated vessel after 90 minutes of ischemia is achieved by a gradual release of the snare to prevent the hyperemic response. A defibrillator is available in the room as are all necessary cardiotonic drugs in the event of cardiac fibrillation or circulatory collapse due to the LAD ligation.

Therapeutic agents are infused in conjunction with reperfusion as follows: bovine superoxide dismutase with approximately 3000 units of activity per milligram assayed by the method of McCord, *J. Biol. Chem.*, Vol. 244, p. 6049 (1969) is obtained from Sigma Chemical Company, St. Louis, MO. It is dissolved in 100 ml of normal saline and infused intravenously over 90 minutes starting 15 minutes before restoration of perfusion. This stimulates the effect which occur during lysis of a coronary thrombus. A solution of copolymer is prepared at 2% weight/volume in saline. It is given intravenously as a bolus over 2 minutes in a dose sufficient to achieve a blood level of 0.6 mg/ml followed by a constant infusion of approximately 25 mg/kg/hour in order to maintain the blood level of approximately 0.6 mg/ml for the remainder of the experiment.

The ethylene oxide-propylene oxide surface active copolymer has the following general formula:

wherein the molecular weight of the hydrophobe ($C_3H_6O$) is approximately 1750 and the total molecular weight of the compound is 8400.

The synergistic effect of the combination is demonstrated by comparing the results of dogs treated with both the copolymer and SOD with those treated with either material alone or no treatment.

Agents are infused intravenously utilizing an IVAC 560 infusion pump. Infusion begins 15 minutes prior to release of the snare and continues until the total dose for each group has been administered. The chest is closed in layers. A chest tube is utilized to evacuate the pneumothorax and is removed when spontaneous respirations resume. I.V. fluids are given (Lactated Ringer's Solution) to compensate for the 24 hour NPO period preceding the operation, in addition to a 3 to 1 ratio to compensate for blood loss. The animals are then maintained and followed closely for the next 24 hours. Each animal is then returned to the operating suite and under general anesthesia the previous incision is reopened. The animal is sacrificed utilizing a barbiturate overdose. The heart and proximal 4 of ascending aorta is excised being sure to include the origins of the coronary arteriesl.

All groups are subjected to the same procedures for identification of the area of the myocardium at risk for infarction and the area actually infarcted.

This technique involves perfusion of the LAD with 2, 3, 5-triphenyltetrazolium chloride (TTC), which stains the intact myocardium red and leaves the infarcted myocardium unstained, The limits of the area of myocardium at risk are determined by perfusing the remainder of the coronary system, via the aortic root, with Evans Blue dye. The area at risk is defined by a lack of Evans Blue stain.

The combination of the surface active copolymer and superoxide dismutase is synergistic in protecting myocardial tissue. The amount of tissue damaged after the ischemic period was significantly less than with surface active copolymer or mannitol alone.

EXAMPLE VIII

A test is performed to demonstrate the ability of the combination of mannitol and an appropriate surface active copolymer to produce greater protection of ischemic myocardium from reperfusion injury associated with oxygen radicals and other factors than mannitol alone.

Under general anesthesia (sodium thiopental 25 mg/kg), the dogs are intubated and ventilated with 70% oxygen at a rate of 12 breaths per minute. A satisfactory level of anesthesia is maintained with intermittent boluses of pentothal as required. After skin preparation, a left anterior thoracotomy is performed, the pericardium incised and the heart exposed. The left anterior descending (LAD) coronary artery is identified, isolated and encircled with a snare 1 cm from its origin. Temporary LAD occlusion is accomplished by tightening the snare and continues for 90 minutes. During the procedure, the heart rate and blood pressure are monitored utilizing a Hewlett-Packard 7758B 8-channel recorder. Arterial blood pressure is monitored through an 18 gauge indwelling catheter in the right femoral artery and measured with a Hewlett-Packard quartz transducer. Electrocardiographic evidence for anteroseptal myocardial ischemia is also monitored. Reperfusion of the ligated vessel after 90 minutes of ischemia is achieved by a gradual release of the snare to prevent the hyperemic response. A defibrillator is available in the room as are all necessary cardiotonic drugs in the event of cardiac fibrillation or circulatory collapse due to the LAD ligation.

Therapeutic agents are infused in conjunction with reperfusion as follows: Two ml/kg of a mannitol solution (12.5 g/50 ml of isotonic saline) (Sigma Chemical Co., St. Louis, MO.) is infused intravenously over 45 minutes starting 15 minutes before restoration of perfusion. This stimulates the effects which occur during lysis of a coronary thrombus. A solution of copolymer is prepared at 2% weight/volume in saline. It is given intravenously as a bolus over 2 minutes in a dose sufficient to achieve a blood level of 0.6 mg/ml followed by a constant infusion of approximately 25 mg/kg/hour in order to maintain the blood level of approximately 0.6 mg/ml for the remainder of the experiment.

The ethylene oxide-propylene oxide surface active copolymer has the following general formula:

wherein the molecular weight of the hydrophobe ($C_3H_6O$) is approximately 1750 and the total molecular weight of the compound is 8400.

The synergistic effect of the combination is demonstrated by comparing the results of dogs treated with both the copolymer and mannitol with those treated with either material alone or no treatment.

Agent are infused intravenously utilizing an IVAC 560 infusion pump. Infusion begins 15 minutes prior to release of the snare and continues until the total dose for each group has been administered. The chest is closed in layers. A chest tube is utilized to evacuate the pneumothorax and is removed when spontaneous respirations resume. I.V. fluids are given (Lactated Ringer's Solution) to compensate for the 24 hour NPO period preceding the operation, in addition to a 3 to 1 ratio to compensate for blood loss. The animals are then maintained and followed closely for the next 24 hours. Each animal is then returned to the operating suite and under general anesthesia the previous incision is reopened. The animal is sacrificed utilizing a barbiturate overdose. The heart and proximal 4 cm of ascending aorta is excised being sure to include the origins of the coronary arteries.

All groups are subjected to the same procedures for identification of the area of the myocardium at risk for infarction and the area actually infarcted.

This technique involves perfusion of the LAD with 2, 3, 5-triphenyltetrazolium chloride (TTC), which stains the intact myocardium red and leaves the infarcted myocardium unstained. The limits of the area of myocardium at risk are determined by perfusing the remainder of the coronary system, via the aortic root, with Evans Blue dye. The area at risk is defined by a lack of Evans Blue stain.

The combination of the surface active copolymer and mannitol is synergistic in protecting myocardial tissue. The amount of tissue damaged after the ischemic period was significantly less than with surface active copolymer or mannitol alone.

EXAMPLE IX

Glass beads (500–750 microns in diameter) are packed into tuberculin syringes and coated with fibrinogen by allowing recalcified citrated human plasma to coagulate and cross-link for 60 minutes at 37° C. Heparinized human blood, diluted 1:3 with normal saline with or without 0.1% surface active copolymer is then added to the reservoir and allowed to pass through the column by gravity at a pressure of 5 cm of water. The volume of blood flowing through the column over 20 minutes is measured.

The surface active copolymer used in this example has the following formula:

$$HO(C_2H_4O)_b(C_3H_6O)_a(C_2H_4O)_bH$$

wherein the molecular weight of the hydrophobe $(C_3H_6O)$ is approximately 1750 and the total molecular weight of the compound is 8400.

Figure 2:
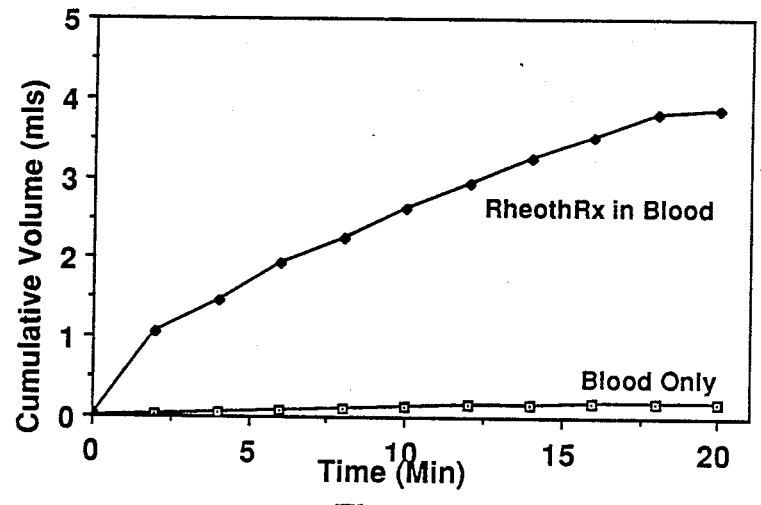
FIG. 2 is a graph showing the effect of the surface active copolymer on flow of blood through a clot.

The results of this Example are summarized in FIG. 2. As can be seen in FIG. 2, only approximately 0.2 to 0.3 mls of blood flowed through the in vitro clot in twenty minutes. However, when the surface active copolymer was added to the blood, the flow of blood through the clot was increased to approximately 4 mls.

EXAMPLE X

The surface active copolymer has a cytoprotective effect. This is shown in the following example. Isolated rat hearts are perfused with packed human red blood cells suspended in Krebs-Henseleit buffer at a hematocrit of 12%.

The surface active copolymer used in this example has the following formula:

$$HO(C_2H_4O)_b(C_3H_6O)_bH$$

wherein the molecular weight of the hydrophobe $(C_3H_6O)$ is approximately 1750 and the total molecular weight of the compound is 8400.

After a period of stabilization, the lines are clamped to produce no flow ischemia for one-half hour. The lines are then reopened to facilitate reperfusion for 10 minutes after which time functional measurements are made and the hearts fixed for histologic examination.

Control hearts reperfused with blood alone recover only 5% of normal function as measured by cardiac output. Histologically, they show widespread contraction bands indicative of myocardial necrosis. In addition, there is extensive sloughing of arteriolar endothelial cells. Hearts treated identically except that the surface active copolymer is added to the blood for the last 10 minutes of the experiment during reperfusion regain 40% of normal function, show much less evidence of contraction band necrosis and preservation of endothelial cells. Under a broad range of experimental conditions, the surface active copolymer can protect myocardial cells from necrosis associated with reperfusion following a degree of ischemic injury which cannot be tolerated by control hearts. The protective effect of the surface active copolymer is greatest when it is added early in the experiment and when conditions of low flow rather than no flow ischemia are used.

EXAMPLE X

Blood was collected using the two-syringe method from healthy volunteers with normal platelet counts and diluted 1:10 with 0.11M sodium citrate. Either the surface active copolymer or normal saline was then gently mixed with the blood. The surface active copolymer was used in final concentration of 0.6 mg/ml and 2.0 mg/ml. Platelet-rich plasma was separated by centrifugation at 200×G for twelve minutes. Platelet-poor plasma was separated by centrifugation at 600×G for twenty minutes. The platelet-rich plasma was stored in polypropylene tubes and continuously agitated for specified periods of time.

The surface active copolymer used in Examples XII through XVI has the following formula:

$$HO(C_2H_4O)_b(C_3H_6O)_a(C_2H_4O)_bH$$

wherein the molecular weight of the hydrophobe $(C_3H_6O)$ is approximately 1750 and the total molecular weight of the compound is 8400.

EXAMPLE XII

In vitro testing of aggregation utilizes an optical aggregometer (Bio-Data Model PAP-2A) and is based on the turbidometric method of Born. Platelet-rich plasma (0.45 ml) is warmed to 37° C. while being agitated continuously with a small magnetic stir bar. Platelet-poor plasma (0.50 ml) is used to blank the platelet-rich plasma. Following the addition of an aggregating reagent (0.05 ml), platelets clump together, causing the turbidity of the platelet-rich plasma to decrease. The turbidity of the suspension is constantly measured by recording transmission of a light beam directed through it, and is recorded as a change in voltage on a chart recorder. The rate of aggregation is dependent on the number of platelets, temperature, concentration of aggregating reagents, calcium, and fibrinogen. Aggregating agents were used at the following standard concentrations unless otherwise indicated: ADP (Dade Cluster Reagent) $2 \times 10^{-5}M$,; Collagen (Dade Cluster Reagent) 200 µg/ml; and, Ristocetin (Bio-Data Corp.) 1.2 mg/ml.

Figure 3:
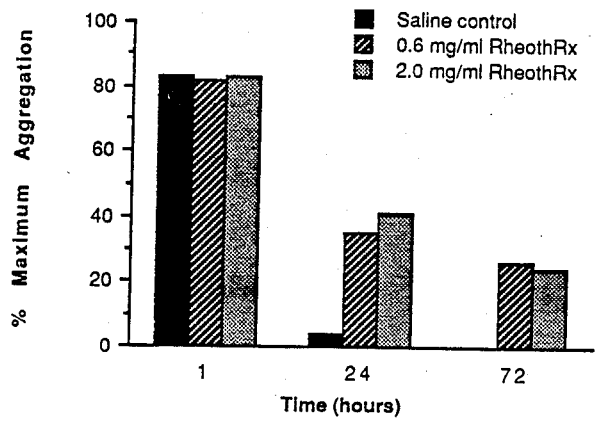
FIG. 3 illustrates the ability of the surface active copolymer to preserve platelet function when using ADP as the agonist.

FIG. 3 illustrates the ability of the surface active copolymer, at both 0.6 mg/ml and 2.0 mg/ml, to preserve platelet function when using ADP at $2 \times 10^{-5}M$ as the agonist. While the percent maximum aggregation is decreased from the immediate analysis, the surface active copolymer platelets retained a substantial amount of activity. The saline control demonstrated either no or very little activity at the 24 and 72 hour assays.

EXAMPLE XIII

Figure 4:
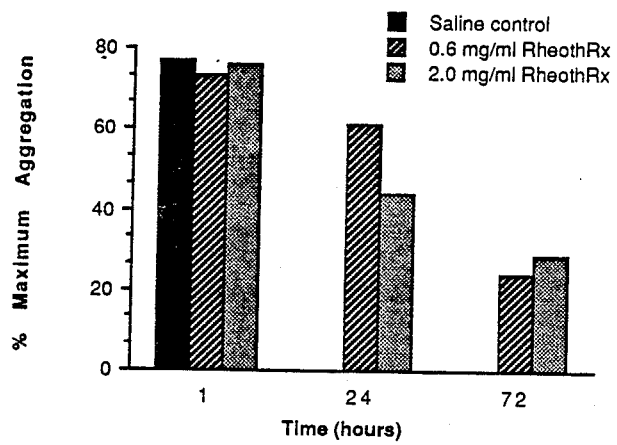
FIG. 4 illustrates the preservation effect of the surface active copolymer on platelets over 24 and 72 hours when using collagen as an agonist.

FIG. 4 illustrates the preservation effect of the surface active copolymer over 24 and 72 hours when using collagen as an agonist. While decreased, platelets stored in the presence of the surface active copolymer still maintains substantial functional activity. The control platelets demonstrate no activity after this prolonged storage.

EXAMPLE XIV

Table C shows the results of several experiments which test the functional ability of platelets at time of collection and, also, at 24 hours storage. The agonist used in this study is ADP at $2 \times 10^{-5}M$. At 24 hours storage, the surface active copolymer at 0.6 mg/ml and 2.0 mg/ml consistently improves the function of the platelets when compared to the saline control.

TABLE C

|  | % Maximun aggregation ± SE | |
|---|---|---|
|  | Immediate | 24 hours |
| Saline control | 89.5 ± 2.4 (n = 4) | 16.5 ± 4.3 (n = 4) |
| RheothRx 0.6 mg/ml | 82.7 ± 2.9 (n = 3) | 51.8 ± 6.2 (n = 4) |
| RheothRx 0.2 mg/ml | 84.0 ± 1.9 (n = 3) | 57.0 ± 5.6 (n = 4) |

EXAMPLE XV

Platelet counts on the platelet-rich plasma samples are conducted in the Hematology Laboratory at Emory University Hospital. The mean platelet volume (MPV) and platelet histograms are also analyzed. This laboratory employs a Coulter Stacker (Coulter Electronics, Hialeah, FL.) in sample analysis. The platelet counts and MPVs remains unchanged in the samples incubated with the surface active copolymer, as shown in Table D below. The control sample lost a substantial number of platelets over the 24 hours. The Coulter Stacker is unable to determine a value for the MPV in the control sample. However, the platelet histogram shows a definite shift to the left, indicating a smaller value for the MPV. The platelet histograms for the surface active copolymer samples are unchanged over this period of time.

TABLE D

|  | Platelets/cumm | MPV |
|---|---|---|
| Immediate | 385,000 | 8.3 |
| Saline control - 24 hrs. | 185,000 | ** |
| 0.6 mg/ml RheothRx - 24 hrs. | 408,000 | 7.8 |
| 2.0 mg/ml RheothRx - 24 hrs. | 414,000 | 8.1 |

EXAMPLE XVI

Two 15 ml polypropylene centrifuge tubes (Becton Dickinson, Lincoln Park, N.J.) are filled with approximately 5 ml of whole blood drawn from a healthy human volunteer. To one of the tubes is added the surface active copolymer with the following general formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is 8400. The final concentration of the surface active copolymer in the blood is approximately 0.67 mg/ml. The tubes are slowly inverted several times over a 5 minute period to be sure that the blood in both tubes is in contact with the sides of the tubes. The tubes are then allowed to stand upright. The blood in the tube without the surface active copolymer uniformly coated the sides of the tube. The tube with the surface active copolymer did not coat the sides of the tube.

It is believed that the blood in the tube without the surface active copolymer coats the sides of the tube because of the adhesion of hydrophobic proteins, such as fibrinogen, to the hydrophobic sides of the tube. However, the blood with the surface active copolymer does not coat the sides of the tube. This is probably because the surface active copolymer blocks the hydrophobic interaction between the hydrophobic proteins present in the blood and the hydrophobic sides of the tube.

EXAMPLE XVII

The surface active copolymer is effective in promoting blood flow in tissue damaged by heat wherein there are increased pathologic hydrophobic surfaces.

The ethylene oxide-propylene oxide surface active copolymer used in this example has the following general formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is 8400.

In this example, the backs of 300 g rats are shaved. The rats are anesthetized and then placed in a plastic frame wherein 36 square centimeter portion of the shaved back is exposed. The exposed tissue is then scalded with boiling water for 10 sec. This treatment causes a full thickness burn on the back. Animals are dryed with a clean towel and placed into individual cages. Within 30 minutes following the burn injury, control rats receive either 10 ml Ip saline or 1 ml IV isotonic saline. Rats that receive the surface active copolymer receive either 10 ml IP surface active copolymer (200 mg/kg in isotonic saline) or 1 ml IV surface active copolymer (50 mg/kg in isotonic saline). After 24 hours, the control rats develop large blisters and have a blanched appearance. The copolymer treated rats show no blisters and the gross abnormalities demonstrated in the control rats are significantly less. This observation is made in both the IV and IP treated rats.

The rats are biopsied 24 hours after the burn. The control rats show severe necrosis in the burn area. The copolymer treated rats show only partial thickness damage and show viable cells in the basal layer of hair follicles. In addition, there is significantly greater blood flow and less loss of fluid in the burned tissue from the copolymer treated rats.

Although not wanting to be bound by the following theory, it is thought that reperfusion injury mediated by granulocyte adhesion-endothelial cell interaction which causes tissue damage was inhibited by blocking pathological hydrophobic interactions thereby preserving endothelial cells, preventing sludging of blood and preventing loss of fluid into tissue and/or other factors.

EXAMPLE XVIII

The ethylene oxide-propylene oxide surface active copolymer used in this example has the following general formula:

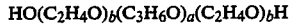

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is 8400.

The surface active copolymer of the present invention has little effect on viscosity of normal blood. However, the surface active copolymer of the present invention does have an effect on blood from a patient undergoing trauma such as an operation. This is shown in the following experiment. Blood from patients about to undergo open heart surgery is collected and blood viscosity at various shear rates is measured both with and without the surface active copolymer present. The surface active copolymer is present in the blood at a concentration of about 0.6 mg/ml.

Figure 5:
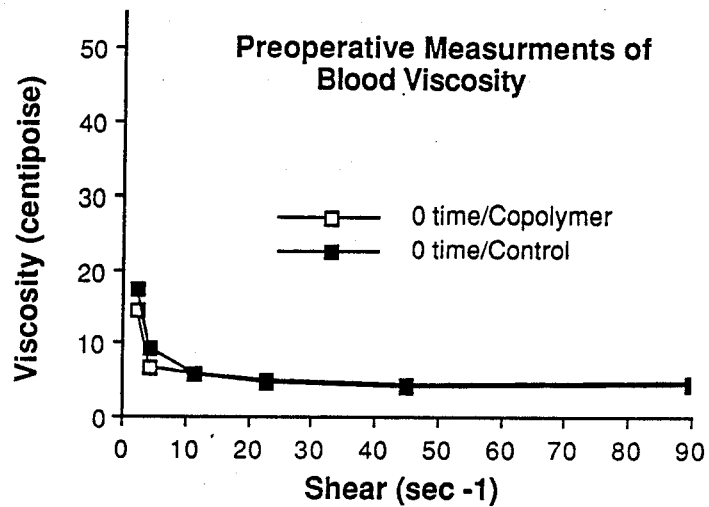
FIG. 5 illustrates the effect of the surface active copolymer on blood viscosity in patients before open heart surgery.
Figure 6:
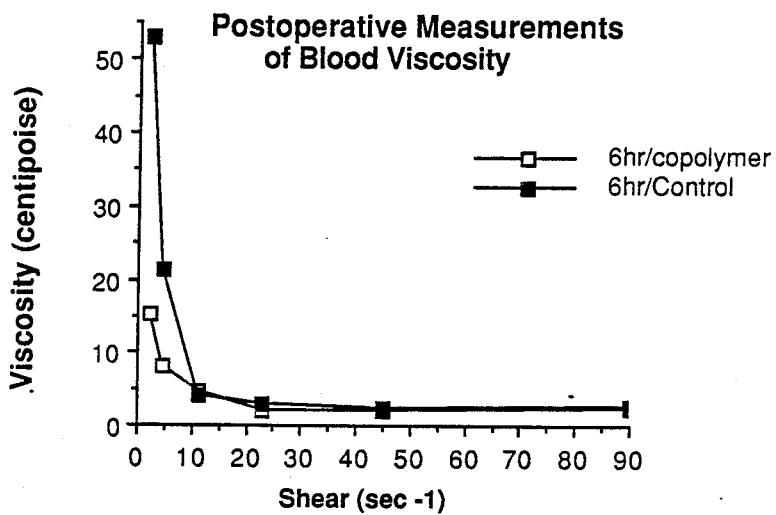
FIG. 6 illustrates the effect of the surface active copolymer on blood viscosity in patients 6 hours after open heart surgery.

FIG. 5 shows the viscosity of the blood from preoperative patients with and without the surface active copolymer. The surface active copolymer has little effect on the viscosity of the blood at all shear rates tested when compared to blood without the copolymer. FIG. 6 shows the viscosity of blood from patients six hours after open heart surgery. As shown, blood from these patients with no copolymer showed a large increase in viscosity at low shear rates. When the copolymer is added to the blood at a concentration of about 0.6 mg/ml, the viscosity at low shear rates is reduced to normal levels.

There was a significant increase in soluble fibrin levels in postoperative patients when compared to preoperative patients. Although not wanting to be bound by the following hypothesis, it is believed that the reduction is viscosity of blood at low shear rates is a result of the copolymer's ability to reduce pathologic hydrophobic interactions in the blood with the high concentration of soluble fibrin. This allows blood to flow more efficiently through the microvasculature.

It should be understood, of course, that the foregoing relates only to a preferred embodiment of the present invention and that numerous modifications or alterations may be made therein without departing from the spirit and the scope of the invention as set forth in the appended claims.

I claim:

1. A method for preserving a suspension of platelets comprising admixing with the suspension of platelets an effective amount of a surface active copolymer with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, and b is an integer such that the hydrophile portion represented by $(C_2H_4O)$ constitutes approximately 50% to 95 % by weight of the compound.

2. The method of claim 1 wherein said surface active copolymer has the following formula:

$$HO(C_2H_4O)_b(C_3H_6O)_a(C_2H_4O)_bH$$

wherein a is an integer such that the hydrophobe represented by $(C_3H_6O)$ has a molecular weight of approximately 1200 to 3500, and b is an integer such that the hydrophile portion represented by $(C_2H_4O)$ constitutes approximately 50% to 95% by weight of the compound.

3. The method of claim 1 wherein said surface active copolymer comprises the following formula:

$$HO(C_2H_4O)_b(C_3H_6O)_a(C_2H_4O)_bH$$

wherein the molecular weight of the hydrophobe $(C_3H_6O)$ is approximately 1750 and the total molecular weight of the compound is approximately 8400.

* * * * *